US008642293B2

(12) United States Patent
Sarofim et al.

(10) Patent No.: US 8,642,293 B2
(45) Date of Patent: *Feb. 4, 2014

(54) DISPOSABLE DEVICE FOR ANALYZING A LIQUID SAMPLE CONTAINING A NUCLEIC ACID WITH A NUCLEIC ACID AMPLIFICATION APPARATUS

(75) Inventors: Emad Sarofim, Hagendorn (CH); Olivier Elsenhans, Sins (CH); Martin Kopp, Cham (CH); Hans-Peter Wahl, Schopfheim (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 559 days.

This patent is subject to a terminal disclaimer.

(21) Appl. No.: 12/373,517

(22) PCT Filed: Jul. 5, 2007

(86) PCT No.: PCT/EP2007/005953

§ 371 (c)(1), (2), (4) Date: Jan. 12, 2009

(87) PCT Pub. No.: WO2008/006502

PCT Pub. Date: Jan. 17, 2008

(65) Prior Publication Data

US 2010/0003683 A1 Jan. 7, 2010

(30) Foreign Application Priority Data

Jul. 14, 2006 (EP) .................................... 06014680

(51) Int. Cl.

*C12P 19/34* (2006.01)
*C12M 1/00* (2006.01)
*C12Q 1/68* (2006.01)

(52) U.S. Cl.

USPC ......................... 435/91.2; 435/283.1; 435/6.1

(58) Field of Classification Search

USPC .......................................... 435/283.1, 91.2, 6
See application file for complete search history.

(56) References Cited

U.S. PATENT DOCUMENTS

| | | | | |
|---|---|---|---|---|
| 5,587,128 | A * | 12/1996 | Wilding et al. | 422/50 |
| 5,666,810 | A * | 9/1997 | Miesterfeld et al. | 60/530 |
| 6,551,841 | B1 | 4/2003 | Wilding et al. | |
| 2002/0055167 | A1* | 5/2002 | Pourahmadi et al. | 435/287.2 |
| 2002/0168298 | A1* | 11/2002 | Huhn et al. | 422/100 |
| 2004/0053290 | A1* | 3/2004 | Terbrueggen et al. | 435/6 |
| 2005/0013732 | A1 | 1/2005 | Battrell et al. | |

FOREIGN PATENT DOCUMENTS

| | | | |
|---|---|---|---|
| EP | 0739423 | B1 | 1/2002 |
| EP | 1179585 | A2 | 2/2002 |
| EP | 1179585 | A3 | 3/2002 |
| EP | 1179585 | B1 | 7/2008 |
| WO | 2004069412 | A1 | 8/2004 |
| WO | 2007005953 | | 11/2007 |

* cited by examiner

*Primary Examiner* — Cynthia B Wilder
(74) *Attorney, Agent, or Firm* — M. Reza Savari

(57) ABSTRACT

The invention is directed to a disposable sample holding and processing device (1) dimensioned for being operated in a nucleic acid amplification apparatus for analyzing a liquid sample containing a nucleic acid by a nucleic acid amplification technique. The device (1) comprises chambers (15, 16) and channels (44) designed to perform the steps of capturing, amplification and detection of the nucleic acid within the device (1), and optionally also a lysis chamber (3). The binding chamber (15) contains a solid phase (14) for immobilization of a component of the sample to be analyzed, and the amplification chamber (16) is connected to the binding chamber (15) by a fluid channel (44). The device (1) comprises a rigid body (42) and at least one channel (44), the binding chamber (15) and the amplification chamber (16) are situated on side-surfaces (50) of the body (42), each of those side-surfaces (50), on which a channel (44), the binding chamber (15) or the amplification chamber (16) is situated, is covered by at least one wall (41) and these side-surfaces (50) are substantially vertical planes when the device (1) is operated in the nucleic acid amplification apparatus.

13 Claims, 10 Drawing Sheets

DISPOSABLE DEVICE FOR ANALYZING A LIQUID SAMPLE CONTAINING A NUCLEIC ACID WITH A NUCLEIC ACID AMPLIFICATION APPARATUS

This application claims the benefit of priority under 35 U.S.C. §119 of EP Application 06014680.0 filed Jul. 14, 2006 the content of which is hereby incorporated by reference.

The invention is directed to a disposable sample holding and processing device for being operated in a nucleic acid amplification apparatus for analyzing a liquid sample containing a nucleic acid by a nucleic acid amplification technique, particularly a Polymerase Chain Reaction Technique (PCR) analysis, more particularly a quantitative real-time-PCR (TaqMan-PCR or Hybridisation-Probe-PCR) analysis.

Such a device is disclosed in U.S. Pat. No. 6,551,841 B1. The known device consists of a substrate of silicon or a polymeric material in which channels and chambers are formed. The substrate is covered by a cover made of glass or plastic which seals the channels and chambers between the substrate and the cover. The device is designed to be used in a horizontal orientation.

The document U.S. Pat. No. 5,587,128 discloses a disposable device comprising an interface between a tip and an integrated device for a PCR-analysis. The tip serves to eject a liquid into a cavity comprising a fluid port.

In the document U.S. Pat. No. 6,664,104 an integrated disposable is disclosed which is used for an integrated process of sample preparation, amplification and detection. The disposable has an opening into which the sample can be pipetted. The reaction chamber has to be closed by a cover.

The document EP 0 884 104 B1 describes a set of a receptacle and a tip. The receptacle is not very advantageous with respect to avoiding contamination.

From the manufacturer Iquum a molecular testing and diagnosis system entitled Liat™ is known comprising a flexible tube as a sample vessel containing all required assay reagents for nucleic acid testing processes, including reagent preparation, target enrichment, inhibitor removal, nucleic acid extraction, amplification and real-time detection in a portable analyzer automatically executing all required assay steps. The assay reagents are pre-packed in tube segments separated by peelable seals arranged in a vertical line. Multiple sample processing actuators are required for compressing the tube, selectively releasing reagents from tube segments and moving the sample from one segment to another. The tube system is a confined closed system approach in the sense that once a sample has been introduced and the tube is capped, the tube remains closed for all test purposes. This is advantageous with respect avoiding cross-contamination and reducing biohazard risks by a safe disposal of the tube after use wherein any biohazardous waste remains enclosed, but it has the disadvantage that no sample reagent or reaction mixture can be added or removed during the process thus making it inflexible.

The technical field of the invention is related to disposable devices used for analyzing a sample with a nucleic acid amplification technique. The purpose of the analysis is the detection (presence or absence of an analyte) and/or the quantification of the concentration of an analyte in a sample. In the current invention the analyte is a nucleic acid: RNA or DNA or derivatives there off. The derivatives (Nucleic Acids) mentioned include molecules which are accessible directly or indirectly (e.g. after chemical modification) to a NA amplification method (e.g. DNA-polymerase, Transcriptase, Reverse-Transcriptase, etc.). The target analytes can be e.g. genetic material with biological origin e.g. for genetic testing, in case of infectious diseases the analyte can be nucleic acid material from a virus or bacteria, in case of gene-expression the analytes can be m-RNAs, the analyte can also be methylated DNA.

EP 1 179 585 A2 discloses an integrated fluid manipulation cartridge for nucleic acid testing which is manually placed in a testing instrument in an inclined direction. The cartridge comprises a fluid interface (sample port) for introducing a fluid sample into the cartridge in a direction perpendicular to the side surface of the cartridge. The sample port is designed for manual sample introduction into the cartridge. The cartridge is neither designed for an automated handling and operation nor for an automated sample introduction of the sample into the cartridge. Further the processing of the cartridge in the testing instruments requires a lot of space due to the inclined orientation of the cartridge in its position of use. The cartridge is highly integrated and complex, comprising analyte-specific reagents preloaded in manufacturing, pressure actuators for processing the fluids in the device and supply chambers with processing liquids, thus making the cartridge rather costly.

In order to analyze large numbers of fluid samples by a nucleic acid amplification technique like PCR speed and cost of an analysis are important aspects of sample holding and processing devices. It is therefore an object of the present invention to provide a disposable sample holding and processing device suitable for analyzing a fluid sample at low cost and within a conveniently short time. Further disadvantages of the prior art to be overcome by the present invention are the aspects of easy manufacturing, easy to use in an automatic processing device, in particular with respect to the aspects of fluid processing including insertion into the disposable and transport and holding of the disposable in the analysis apparatus, the space required by the disposable in the analysis apparatus, the avoiding of biohazard risks and cross-contamination and the integration of functions in the disposable.

These objects are solved according to the invention by a disposable sample holding and processing device dimensioned for being operated in a nucleic acid amplification apparatus for analyzing a liquid sample containing a nucleic acid by a nucleic acid amplification technique, wherein the device is a fluidic device comprising chambers and channels designed to perform the steps of capturing, amplification and detection of the nucleic acid amplification analysis by using a method for nucleic acid amplification within the device, the device comprises a binding chamber containing a solid phase for solid phase extraction of a component of the sample to be analyzed, and the device comprises an amplification chamber connected to the binding chamber by a fluid channel, the device comprises a rigid body and at least one channel, the binding chamber and the amplification chamber are situated on side-surfaces of the body, each of those side-surfaces, on which a channel, the binding chamber or the amplification chamber is situated, is covered by at least one wall, and wherein these side-surfaces are substantially vertical planes when the device is operated in the nucleic acid amplification apparatus, the device is designed to be operated in the nucleic acid amplification apparatus with the side-surfaces being substantially orientated in a vertical plane and wherein the device comprises at least one fluid interface connected by a fluid channel to at least one chamber of the device, preferably to one of the binding chamber and the amplification chamber, wherein the fluid interfaces are situated on top- and/or bottom-surfaces of the body when the device is operated in the nucleic acid amplification apparatus.

As a general rule nucleic acid amplification techniques require subsequent sample processing in different chambers or different stations of a corresponding nucleic acid amplification apparatus. As suggested in U.S. Pat. No. 6,551,841 B1 the sample is processed in a device having a main plane that is a horizontal plane when it is operated in the apparatus for processing. Although support of the device in the apparatus or supply and removal of liquid can be achieved in this manner it has turned out that the overall handling of such a device is difficult and place and time consuming, particularly in an automatic apparatus realizing many steps of the steps for a nucleic acid amplification detection of a sample. The interacting means of the analysis apparatus in which the device is operated can not be shared simultaneously with other devices, because they have to be attached to the device during the analysis.

In contrast, the handling of a disposable device according to the present invention can be easier and less place and time consuming in the corresponding analysis apparatus, particularly when the disposable device according to the invention is provided with integrated diagnostical biochemical functionality according to preferred embodiments of the invention. The disposable device according to the invention can be handled and operated in an easy and automated manner by the nucleic acid amplification apparatus with handling and operation means for inserting the device in a receptacle or seat and loading fluid like the sample fluid into the device in a vertical direction. By this a reliable automated operation, a cost saving high automated throughput and a space-saving design are achieved. The device is preferably not highly integrated and complex, comprises preferably no analyte-specific reagents preloaded in manufacturing or pressure actuators for processing the fluids in the device or supply chambers with processing liquids, but comprises fluid ports for providing selected reagents and fluids to the device upon use and interfaces for processing thus rendering the device both cheap in production and a generic device which can be used in many different analyses. The resources of highly precise interface and actuation means of the analysis apparatus can be shared for a generic type of device.

With respect to advantageous features and embodiments of a nucleic acid analysis apparatus suitable to be used in combination with a disposable device described in the present application reference is made to the simultaneously filed international patent application of the same applicants by the same representative, with the title “Apparatus for performing nucleic acid analysis”, attorneys reference RDG 167/00/WO, corresponding to European patent application EP 06 014 681.8, the disclosure of which application is incorporated herewith by reference.

Further details and advantages of the present invention are illustrated in the following based on an exemplary embodiment making reference to the attached drawings. The following is depicted in the figures.

Figure 1:
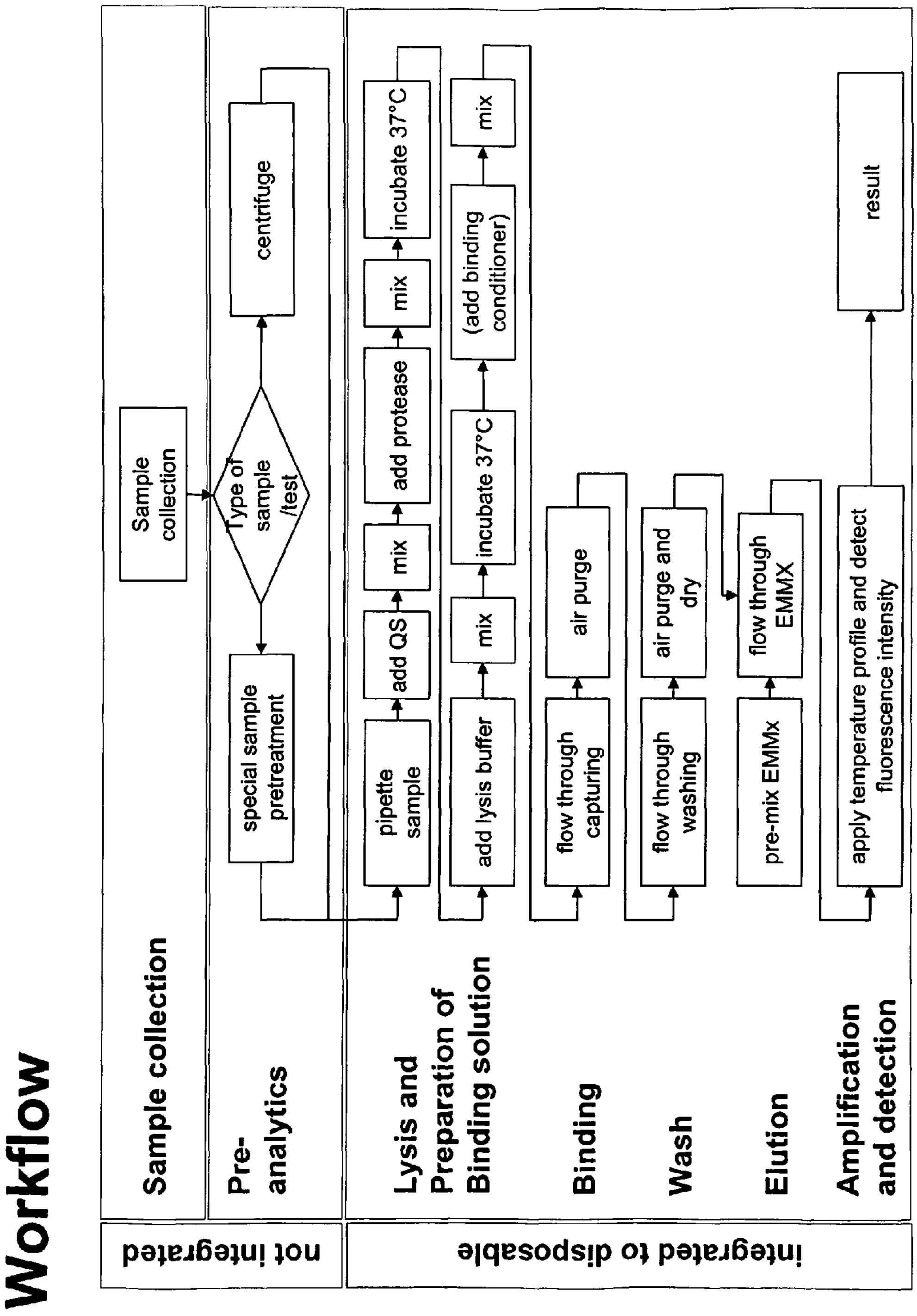
FIG. 1 shows a general workflow overview of a nucleic acid amplification analysis.

The procedure presented in FIG. 1 is a typical procedure for nucleic acid testing (NAT) of a sample comprising a nucleic acid (NA) which may be performed with a preferred embodiment of a disposable according to the invention. Most NA analyses (e.g. using the PCR), analyzing the NA in a biological sample, require that the NA is isolated from other components prone to interfere with the detection reaction of the NA. This first step of isolating the NA, is generally called “sample preparation”. Typical methods for sample preparation are state of the art. A common method is the solid phase extraction of the NA. In this case NAs bind under high concentrations of a chaotropic salt to glass surfaces, while disturbing material from the sample remains in solution.

After binding of the NA to the solid-phase, the solid phase is washed to remove remaining material from the solid-phase, while the NA stays adsorbed. After this wash step of the solid-phase, depending on the inhibiting properties of the wash buffer, the wash buffer has to be removed or otherwise neutralized or reduced to non inhibiting amounts. After this step, the NA is eluted (i.e. dissolved from the solid phase) into a low concentration salt buffer or pure water. This eluate (containing the purified NAs) is generally conform with many NA detection chemistries/assays, e.g. PCR or other linear or exponential NA amplification- and detection methods.

In a sample collection step a sample is taken where the searched NA is expected to be present. Such sample material can be tissue, blood, urine, sputum. The sample depends on the kind of analyte searched. The method of sampling for NA-testing is state of the art, and depends on the analyte and the place of where the sample is present. For example in the case of testing for viruses as HBV, HCV or HIV in blood approximately 3 ml blood is drawn from a human to be tested into a blood collection tube (e.g. Becton Dickinson, with EDTA anticoagulant).

A preanalytics step is performed depending on the sample, analyte and side conditions. Prior to loading the sample to an automated apparatus being able to carry out the automated NA analysis, the sample may has to go to a “pre analytic” step. This preanalytic step mainly covers all steps which make the sample ready to the automated steps on a NA analyzer apparatus. Such preanalytic steps can include for example Homogenization, e.g. of tissue, making the tissue accessible to the following NA procedures, Separation, e.g. separation of erythrocytes from blood, Suspending, e.g. suspending bacteria and viruses in a liquid medium, Grinding, e.g. of plant seeds, for example for genetic testing.

The procedures of such pretreatments are state of the art. An example is that for virus-testing a separation of the red blood chambers from the drawn blood sample according to the recommendations of the sample collection tube (e.g. Becton Dickinson) is performed.

The further analysis steps of FIG. 1 are preferable performed with an automatic nucleic acid amplification and analysis apparatus with a preferred embodiment of a disposable according to the present invention. For this purpose the automated analysis apparatus is manually or automatically loaded with all required material which is used for the analysis. Such materials to be loaded on the instrument may be samples to be analyzed, integrated disposables for carrying out the analysis, which are used for one single assay or part of the assay and which are discharged to the waste after use, and reagents used to run the instrument e.g. system fluid, system wash buffer, and reagents used for the assay, e.g. sample preparation reagents and detection reagents.

The sample can get loaded in a sample collection tube or in special tubes/containers. Disposables are preferably loaded in racks or holders on the apparatus. One single assay may use one single or several different or equal disposables. Such a disposable can be an integrated disposable, wherein integrated means that a number of functions used for one assay are provided in one disposable unit, optionally having several subunits, or a set of several equal or unequal disposables are provided, e.g. if required comprising disposable tips.

Reagents to run the apparatus, e.g. system wash buffers, system fluid, etc, are preferably provided in larger amounts, able to run the instrument at least one day. Such reagents can be diluters, digesting agents (e.g. proteinase or lysing buffers), conditioners (e.g. for adjusting binding conditions), wash-buffers for cleaning a solid-phase, standards (as internal control or for quantification), detection reagents, etc. Reagents used for the disposable itself can get loaded in form of a reagent kit containing all reagents to run one single disposable or in kits allowing many disposables.

Material can be identified by barcode or other identification means for automation reasons. An example of a material to be loaded on an automated NA-apparatus for analyzing HBV-Virus in a human plasma comprises the following:

Sample: At least 1 ml sample (EDTA-Plasma) provided in a tube, identified by a bar-code. For control reason or performance studies the sample can get spiked with HBV viruses provided e.g. from the company Acrometrix (e.g. 1 ml sample spiked with 10'000 copies of HBV virus).

Reagents:

| | | |
|---|---|---|
| | System-/wash fluid | |
| 0.4 | ml | Octan-1-ol |
| 0.3 | g | Trion X100 |
| 0.01 | g | Sodium Azide |
| 0.1 | mMol | Phosphat-buffer pH 7.4 |
| 1 | mMol | Sodium Chloride |
| 1.000 | L | System-/wash fluid (completed with water) |
| | Lysisbuffer | |
| 5.5 | Mol | Guanidinium-rhodanid |
| 0.04 | Mol | TRIS pH 7.4 |
| 9 | g | Triton X100 |

-continued

| | | |
|---|---|---|
| 0.02 | Mol | 1,4-Dimercapot-2,3-butandiol (DTT), threo |
| 14 | mg | polyA (Amersham Sciences) |
| 1.000 | L | Lysisbuffer (completed with water) |
| | Wash buffer | |
| 200 | g | Water |
| 10 | mg | polyA (Amersham Sciences) |
| 0.16 | g | Triton X100 |
| 0.66 | mMol | TRIS pH 7.5 |
| 570 | g | Ethanol |
| 30 | g | Isopropanol |
| approx 1.0 | L | Wash buffer |
| | Proteinase: Reagent used from the Roche Diagnostics Taqman ® HBV Kit | |
| Kit-No: | | 03370194 190 |
| Cassette-No: | | 00058005073 |
| Reagent-No: | | 03 359 026-102 |
| Identifier: | | Pase |
| | QS (Quantification Standard): Reagent used from the Roche Diagnostics Taqman ® HBV Kit | |
| Kit-No: | | 03370194 190 |
| Cassette-No: | | 00058005076 |
| Reagent-No: | | 0058004657 |
| Identifier: | | QS |
| | Elution buffer | |
| 50 | mg | Dodecyl-beta-maltoside (Fluka, PN 44205) |
| 3.3 | mMol | TRIS pH 7.5 |
| 5 | mg | polyA (Amersham Sciences) |
| 1.000 | L | Elution buffer (completed with water) |
| | Mastermix A (Mn): Reagent used from the Roche Diagnostics Taqman ® HBV Kit | |
| Kit-No: | | 03370194 190 |
| Cassette-No: | | 00058005076 |
| Reagent-No: | | 0058004402 |
| Identifier: | | Mn |
| | Mastermix B: Reagent used from the Roche Diagnostics Taqman ® HBV Kit | |
| Kit-No: | | 03370194 190 |
| Cassette-No: | | 00058005076 |
| Reagent-No: | | 0058004403 |
| Identifier: | | Mastermix |
| | Combined Elution Mastermix ("EMMx") - Mixed prior to use | |
| 0.5 | ml | Elution buffer |
| 0.15 | ml | Mastermix A (Mn) |
| 0.35 | ml | Mastermix B |
| 1 | ml | EMMx |

Figure 2:
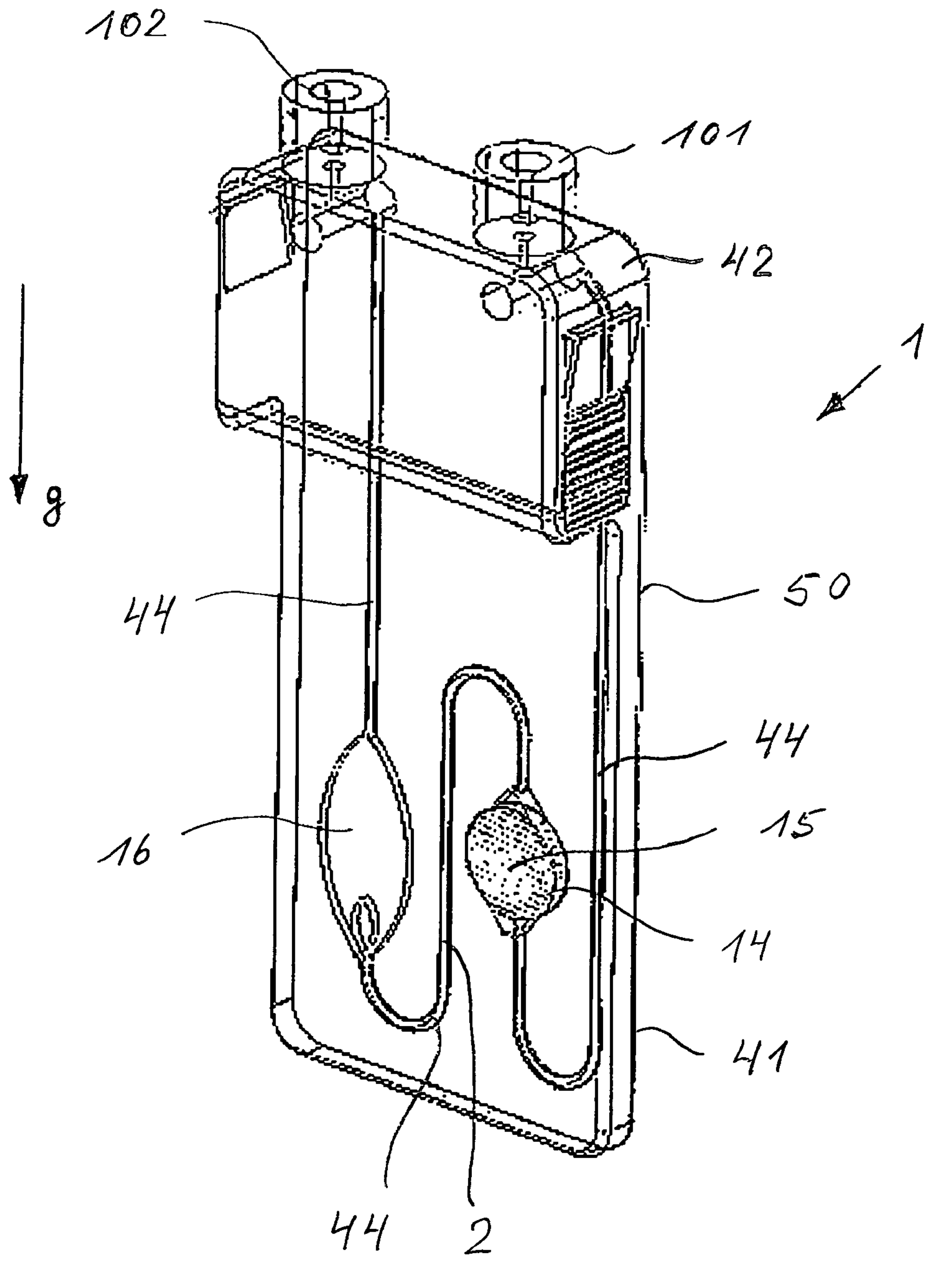
FIG. 2 shows a perspective view of a first embodiment of a disposable according to the invention.
Figure 3:
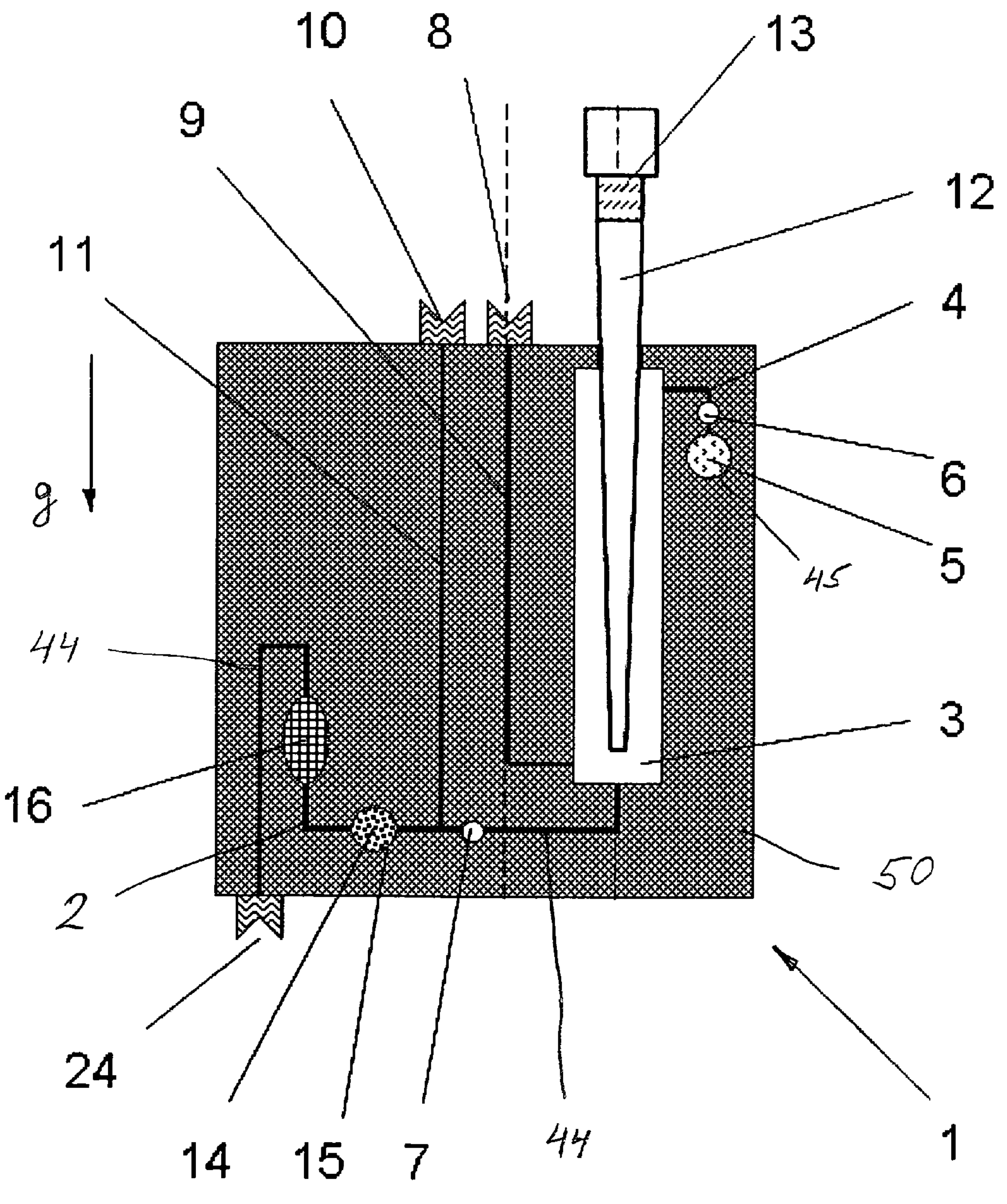
FIG. 3 shows a schematic front view of a second embodiment of a disposable according to the invention.
Figure 4:
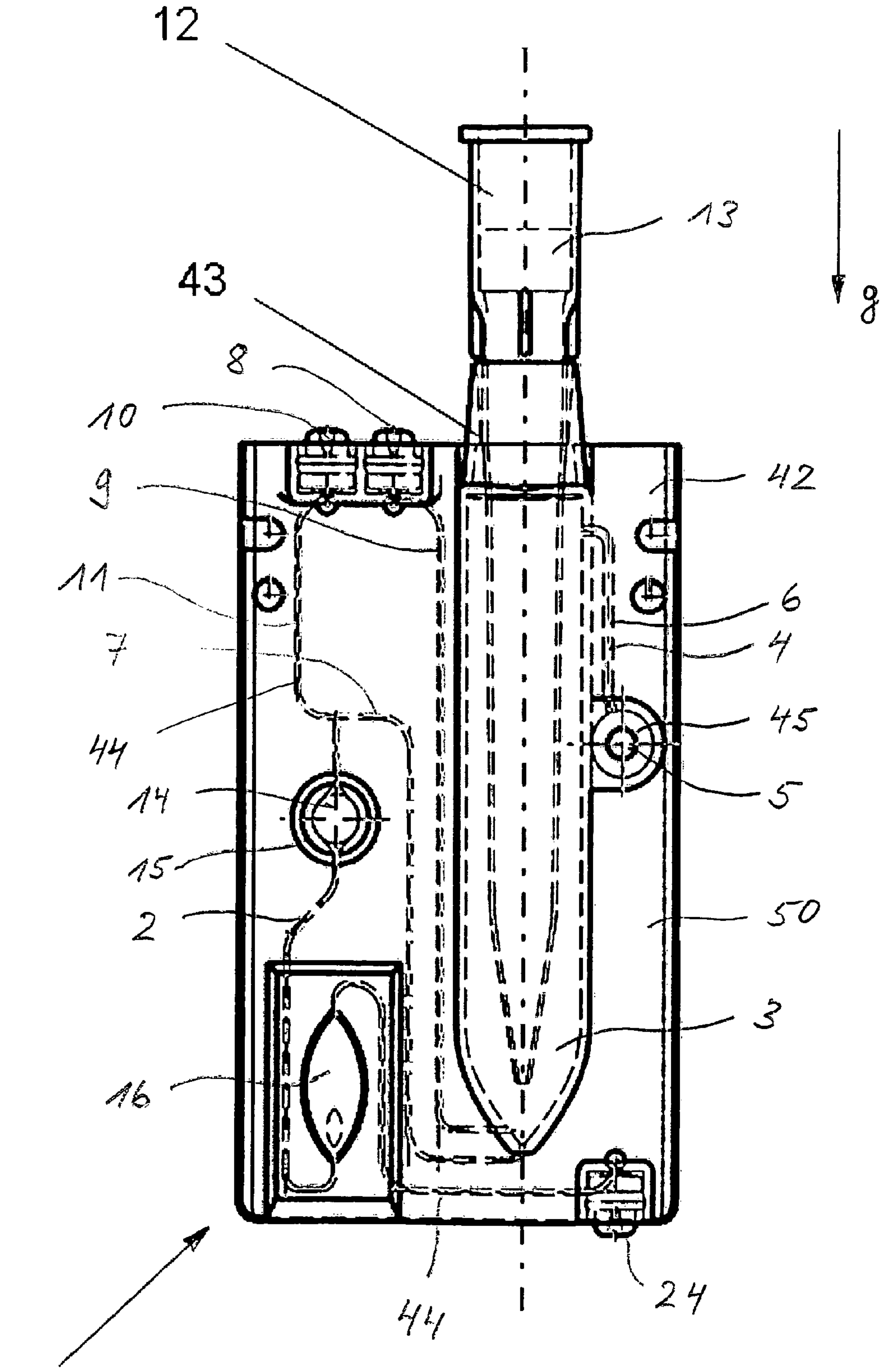
FIG. 4 shows a front view of a more detailed embodiment of the disposable according to FIG. 3.
Figure 5:
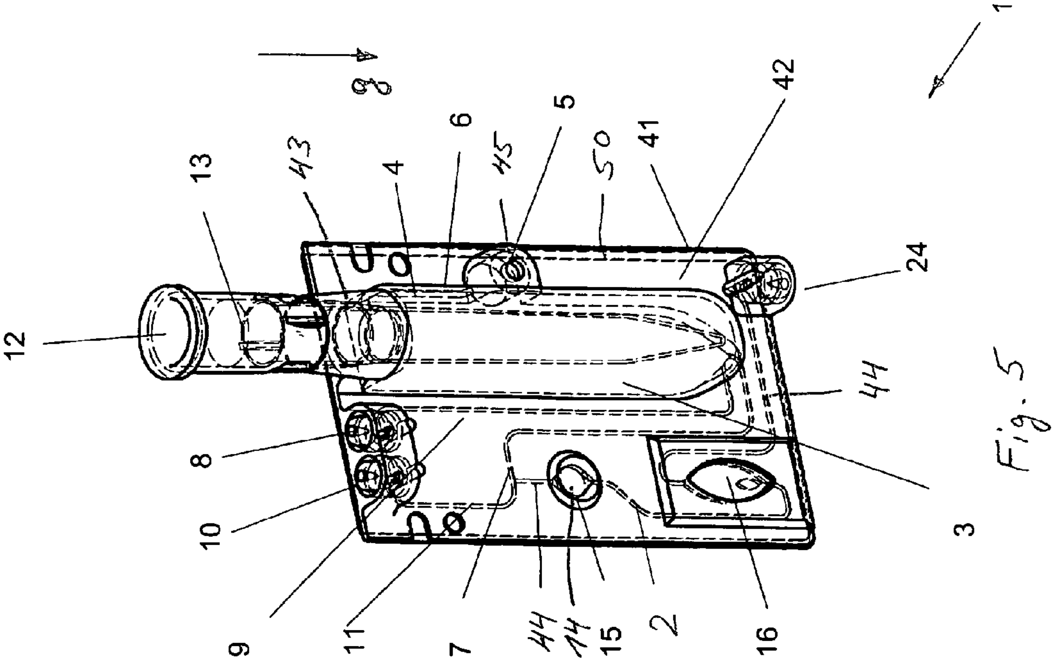
FIG. 5 shows a more detailed perspective front view of the disposable according to FIG. 3.

FIG. 2 shows a perspective view of a first embodiment of a disposable 1 according to the invention. It is a functional integrated and miniaturized chip with an inserted glass fiber fleece 14 and interfaces for fluids and is suitable for integrating the steps of capturing, amplification and detection. It comprises a fluidic supply port, inlet 101, a fluidic removal interface, outlet 102, a binding chamber 15, an amplification and detection chamber 16 and channels 44. The disposable sample holding and processing device 1 is dimensioned for insertion into and being operated (processed) in a nucleic acid amplification apparatus for analyzing a liquid sample containing a nucleic acid by a nucleic acid amplification technique. Also a heat transfer wall 41 and a light transparent wall located above the amplification chamber 16 can be seen.

The device 1 is a fluidic device comprising chambers and channels 44 designed to perform the steps of capturing, amplification and detection of the nucleic acid amplification analysis within the device, comprising a binding chamber 15 containing a solid phase 14 for immobilization/solid phase extraction of a component of the sample to be analyzed, and an amplification chamber 16 connected to the binding chamber 15 by a fluid channel 2. The binding chamber 15, the fluid channel 2 and the amplification chamber 16 of the device 1 are situated on a side-surface 50 of the body 42, namely the back-side in FIG. 1, and that side-surface 50, on which the channels, the binding chamber 15 and the amplification chamber 16 are situated, is covered by at least a wall 41. The side-surface 50 is a substantially vertical plane, see the direction of gravity g in FIG. 1, when the device 1 is operated in the nucleic acid amplification apparatus.

The vertical side-surface 50 may be considered to be a "main plane" of the device 1. According to the invention it is not required that the complete channel 44 is located in the main plane, in some embodiments it may be sufficient that e.g. at least the channel 2 connecting the amplification chamber 16 to the binding chamber 15 is arranged in that plane.

The amplification chamber 16 of device 1 of FIG. 2 comprises on one side a transparent optical measurement window for optical detection of the analysis signal and on another side a heat transfer wall 41 having a good thermal conductivity for providing a direct or indirect thermal contact between a temperature control means of the nucleic analysis apparatus and the amplification chamber 16 for heating and/or cooling of a sample in the amplification chamber 16 of the device 1 when it is operated in the nucleic acid amplification apparatus.

The disposable 1 may be a 1-compound with assembled elastomeric inlets 101 and outlets 102 or a 2-compound injection molded body with thermo-plastic elastomeric septa. The back side may be heat sealed with a polypropylene/aluminum foil. The disposable 1 has a layout which is applicable to mass production at low cost. It allows a simple automation of the processing in a nucleic acid amplification apparatus leading to cost reductions and smaller apparatus dimensions. It is flexible in respect to an accommodation to various process versions in respect to workflow, sample-volume and target-analyte, has a high analytical performance provides a fast high reliability of the processing and test results. It is very suitable for an easy automation, increasing the reliability of the apparatus, and provides an easy handling by the customer. Because it is self-contained it is cross-contamination save and save to operate for the ambient.

FIGS. 3 to 9 illustrate further embodiments of disposables 1 according to the invention. The disposables are a functional integrated and miniaturized chip with an inserted glass fiber fleece and interfaces for fluids and are suitable for integrating the steps of lysis, capturing, amplification and detection, i.e. it is an "all-in-one" disposable. The disposable sample holding and processing device 1 is dimensioned for insertion into and being operated in a nucleic acid amplification apparatus, which performs both the steps of nucleic acid extraction and nucleic acid amplification for analyzing a liquid sample containing a nucleic acid by a nucleic acid amplification technique.

The device 1 is a fluidic device comprising chambers and channels designed to perform the steps of capturing, amplification and detection of the nucleic acid amplification analysis within the device, comprising a binding chamber 15 containing a solid phase for immobilization of a component of the sample to be analyzed, and an amplification chamber 16 connected to the binding chamber 15 by a fluid channel 2. The binding chamber 15, the fluid channel 2 and the amplification chamber 16 of the device 1 are situated on a side-surface 50 of the body 42 and that side-surface 50, on which the channels, the binding chamber 15 and the amplification chamber 16 are situated, is covered by a wall 41. The side-surface 50 is a substantially vertical plane, see the direction of gravity g in the figures, when the device 1 is operated in the nucleic acid amplification apparatus. The vertical side-surface 50 may be considered to be a "main plane" of the device 1.

According to a preferred embodiment of the invention the channels 44, the binding chamber 15 and the amplification chamber 16 of the device 1 are formed by cavities being recesses in the body 42 on the side-surfaces of the body 42 and the cavities are covered by the at least one wall 41. Such embodiments can be easily manufactured. The cavities can be preferably situated on opposite side-surfaces of the device 1, which is more preferably with respect to the manufacturing process.

In the figures most preferred embodiments are shown in which most or all cavities are situated on one side-surface 50, i.e. the binding chamber 15, the fluid channel 2 connecting the amplification chamber 16 to the binding chamber 15 and the amplification chamber 16 of the device 1 are located on one surface-side of the body 42 and are covered by a common wall 41. That common wall 41 may be considered to be arranged in a main plane of the device 1 and that plane being a vertical surface-plane 50 of the body 42 when the device 1 is operated in the nucleic acid amplification apparatus.

According to another preferred embodiment of the invention the device 1 comprises at least one fluid interface connected by a fluid channel 44 to at least one chamber of the device 1, preferably to one of the binding chamber 15 and the amplification chamber 16, wherein the fluid interfaces are situated on top- and/or bottom-surfaces 52, 53 of the body 42 when the device 1 is operated in the nucleic acid amplification apparatus. The fluid interfaces may be for supply or removal of fluids used in the analysis performed with the device 1. The fluid interfaces are preferably to be contacted by fluid delivery and/or fluid removal means of the nucleic acid amplification apparatus, wherein the fluid delivery and/or fluid removal means are adapted to supply to and/or to remove from the device 1 a fluid in a vertical direction of flow. Such fluids can be a gas or a liquid, and the liquid can e.g. be a sample or a reagent. According to preferably embodiments the devices 1 comprises at least two fluid supply interfaces, a first for supplying a sample to the device 1 and a second for supplying a reagent to the device 1.

For easy operation of the device 1 in the apparatus it is preferred when the fluid interfaces are constructed such that a supply is on the top surface 52 of the device 1 in a downward direction of flow and the removal is at a bottom surface. Generally it may be preferable when at least one fluid supply interface 8, 10 of the device 1 are constructed such that a fluid can be supplied to the device 1 from above the device 1 in a downward direction.

The individual elements of device 1 are described as follows.

The integrated disposable 1 is a device for performing a Nucleic Acid Test (NAT). The integrated disposable 1 contains a number of integrated elements required to perform a number of procedures required for NAT. Such functions are e.g. chambers for lysis of material, means for diluting and mixing, means performing incubation steps, means for solid phase 14 adsorption, means for fluid transport and/or means for amplification and/or detection steps. The integrated disposable 1 is typically made out of a rigid body 42 forming a substrate of the device 1, which defines chambers, mechanical, fluidic and optical interfaces and a second heat transferring wall 41 joined to this body 42. The body 42 has typically an outer volume between 0.5 ml and 50 ml. Most preferred in a range of 2 ml and 20 ml.

The disposable 1 has a layout which is applicable to mass production at low cost. It allows a simple automation of the processing in a nucleic acid amplification apparatus leading to cost reductions and smaller apparatus dimensions. It is flexible in respect to an accommodation to various process versions in respect to workflow, sample-volume and target-analyte, has a high analytical performance provides a fast high reliability of the processing and test results. It is very suitable for an easy automation, increasing the reliability of the apparatus, and provides an easy handling by the customer. Because it is self-contained it is cross-contamination save and save to operate for the ambient.

At least one wall is joined to the body 42 by appropriate joining techniques. Typical techniques are ultrasound joining, thermal sealing, laser welding, and gluing. Other elements of the integrated disposable 1 may inserted or plugged in to appropriate openings in the body 42. Parts of the disposable may be also made in a 2 compound injection molding process The channels 44 for fluid transport and chambers for accommodating fluid are formed between the body 42 and the heat transferring wall 41.

The lysis chamber 3 is a chamber within the integrated disposable 1 and has preferably at least one heat transferable wall. The volume of the lysis chamber is typically within a range of 50 μl and 20 ml, most preferred in a range of 100 μl and 10 ml.

The lysis chamber 3 is a sample preparation chamber suitable for performing the step of lysis of the nucleic acid analysis within the device, in addition to the embodiment shown in FIG. 2. The sample preparation chamber comprises an opening adapted to receive a sample transfer tip 12 for transferring liquid into the device 1. According to a preferred embodiment the sample preparation chamber 3 is situated on a side-surface 50 of the body 42 and is formed by a cavity being a recess in the body 42, and that side-surface 50 being covered by a wall 41, which wall 41 is substantially a vertical plane when the device 1 is operated in the nucleic acid amplification apparatus. Accordingly, the outlet of the sample preparation chamber 3 may be located in the "main plane" of the device 1 or in a plane parallel to the main plane of the device 1 in order to achieve a small footprint of the device 1.

According to a preferred embodiment which is advantageous in practice the volume of the sample preparation chamber (lysis chamber 3) is much larger than the volume of the amplification chamber 16, the sample is kept and located in the lower end of the sample preparation chamber by gravity and may be transported through the binding chamber 15, the fluid channel 44 and the amplification chamber 16 upon use of the device in a nucleic acid amplification apparatus by a pressure difference between an inlet of the device 1, particularly the sample preparation chamber, and an outlet of the device, the pressure difference being applied to the device by the nucleic acid amplification apparatus.

The pressure difference may be a pneumatic or hydraulic pressure difference. The pressure difference may be applied to the device 1 by applying atmospheric pressure or overpressure to the inlet side of a chamber or fluid channel of the device 1. The pressure difference may be also applied to the device 1 by applying negative pressure or vacuum to the outlet side of a chamber or fluid channel of the device 1.

The lysis chamber 3 venting system 4 is a fluidic connection between the lysis chamber 3 and the ambient allowing gas exchange. The lysis chamber 3 venting system consists typically of a channel 44 with a cross section between 0.01 $mm^2$ and 10 $mm^2$, most preferred between 0.04 $mm^2$ and 2 $mm^2$.

For contamination save operation there can be a lysis chamber venting filter 5 within the fluidic path of the lysis chamber venting system 4. Such filters are commonly known, e.g. from contamination save disposable pipetting tips. Such filters consist typically from a porous material, e.g. cellulose or from a porous polymer. A typical filter area is in a range of 1 $mm^2$ to 500 $mm^2$, most preferred 10 $mm^2$ to 100 $mm^2$.

The venting sealing point 6 is located in a section of a channel, where the channel has to be closed at a certain point of the process. The venting sealing point 6 is typically a section of a channel formed between the two layers body 42 and heat transfer wall. The venting sealing point 6 is located in the lysis chamber venting system 4.

The closing sealing point 7 is located in a section of a channel, where the channel has to be closed at a certain point of the process. The sealing point is typically a section of a channel formed between the two layers: body 42 and heat transfer wall. The closing sealing point 7 is located in the fluidic connection between the lysis chamber 3 and the binding chamber 15.

In general terms it may be preferred when the body 42 of the device 1 comprises a sealing point 6, 7 located close to a channel 44 of the device 1, said channel 44 leading from a chamber of the device 1 to an inlet port 8, 10, outlet port 24 or venting port 45 of the device 1, or leading from a first chamber (e.g. the lysis chamber 3) to a second chamber (e.g. the amplification and detection chamber 16), wherein the channel 44 located close to the sealing point 6, 7 can be (reversibly or irreversibly) sealed by a sealer of the nucleic acid amplification apparatus, e.g. a thermal actuator which may for example be a linear actuated heated piston in order to close said channel 44 for interrupting a flow of liquid or gas through said channel 44 by deforming the channel in its width and thereby sealing together opposite walls of the channel.

To inhibit the flow through an open channel 44, the channel may be closed by thermally sealing off the channel, by means of a channel sealing equipment of the analysis apparatus, i.e. the sealer. For closing channels, channels may be sealed thermally. Under elevated temperature a section in the channel (the sealing point 6 or 7) is compressed or deformed and the open fluid path is closed and sealed together. The channel sealing equipment may consist of a heated piston (regulated to a temperature between 200° C. and 400° C., most preferred from 250° C. to 350° C.), and an actuator able to press the piston towards the sealing point 6, 7 on the integrated disposable 1. The distance of actuation is typically in the range of 0.1 mm to 20 mm, more preferred in a range of 0.2 mm to 3 mm. The force exerted on the disposable 1 may be in the range of 1 N to 100 N, most preferred in range of 2 N to 20 N. The piston may have an active sealing area between 0.5 $mm^2$ and 10 $mm^2$, most preferred from 1 $mm^2$ to 3 $mm^2$ and is adapted to the diameter and shape of the sealing point.

The first fluid port 8 and the second fluid port 10 are interfaces on the integrated disposable 1 by which reagents and optional process gases are delivered to the inside of the integrated disposable 1. The fluid ports 8, 10 are preferably a septum, made of an elastomere. The septum can be pierced by a fluid delivery device, e.g. a reagents pipetting tip 28. The elastomere has a Shore A hardness between 10 und 100 Shore, most preferred between 30 and 60. The thickness in the dimension where the septum is pierced can be in a range of 0.4 mm to 12 mm, most preferred in a range of 2 to 8 mm. The diameter of the septum is in the range of 2 mm to 12 mm, most preferred in the range of 3 mm to 8 mm.

The fluidic connection 9 is channel 44 leading to the lysis chamber 3 starting at first fluid port 8. The fluidic connection 11 is channel 44 leading to the binding chamber 15 starting at second fluid port 10. In order to avoid backflow, outflow of liquid from the binding chamber 15 through the fluidic connection 11 or compression of fluid up to the fluid connection 11 the length of the corresponding channel 44 may be enlarged by not taking a short or direct way, e.g. by giving the channel a meander line.

The (disposable or single-use) sample pipetting tip 12 is common state of the art. It can hold a liquid volume between 10 μl and 10 ml, more preferred between 20 μl and 5 ml and most preferred between 50 μl and 3 ml. The diameter of the opening, at the side where the tip 12 dips into a sample and where the sample is aspirated has an open diameter of 200 μm to 2,000 μm, most preferred a diameter in a range of 400 μm to 1,000 μm. The open diameter where the tip is connected to a tip gripper has a diameter in a range of 2 mm to 20 mm. The tip 12 may have on its outer, upper region a section where the tip 12 forms a sealing zone 43 with the body 42. At the upper end the tip 12 has an interface that is tightly connectable to a tip gripper. Due to the contact with sample and reagents the material of the tip 12 has to be inert to the NAT-assay. A most preferred material is a thermoplastic polymer. Most preferred polymers are polyethylene and polypropylene.

A tip filter 13 may be integrated to the tip 12 to avoid e.g. carry-over by aerosols. The filter 13 will inhibit such undesired mass transport by filtration or retention. The tip filter 13 is typically plugged into the tip 12 and has typically a cylinder like shape. The diameter of the filter is selected to give a tight fitting between the inner wall of the sample pipetting tip 12 and the filter 13. Typical materials for this filter 13 are sintered porous thermoplastic polymers, or fiber based filters (fibers e.g. from cellulose, glass, or polymeric fibers). When required also combinations of materials may be used.

The solid phase 14 is a piece of material with selected material properties. A key material property is its ability to be used for the purification process of the nucleic acids from the matrix. The material must be able to adsorb/desorb respectively bind/release nucleic acids under set conditions. By changing the ambient conditions the nucleic acids are either selectively adsorbed or bound, respectively by changing the conditions the NA are desorbed or released.

A common used system uses as solid-phase silica, and for the adsorption of the nucleic acids, the nucleic acids are brought in contact to the solid phase 14, while the nucleic acids are dissolved in a solution of high salt concentration (e.g. in a 4 Molar Guanidinium chloride solution). For desorption of the nucleic acids bound on the solid phase 14 they have to be brought in contact with an elution buffer of low salt content. The selection of the solid-phase, the binding and elution conditions are broadly described in the literature.

The amount of solid phase 14 used in a disposable 1 is defined by the specific binding capacity of a selected solid phase 14 material and the required binding capacity used in the application. For example a glass fiber fleece made of fibers from CAS 65997-17-3, with a weight of 50 to 800 g/m$^2$ and an uncompressed thickness of 100 μm to 10 mm may be used. Most preferred 100 g/m$^2$ to 400 g/m$^2$ and a thickness of most preferred 200 μm to 5 mm is used. Typically a diameter of 1 mm to 20 mm, most preferred of 3 mm to 12 mm is used. But also another material may be used, e.g. a sintered solid phase, in another shape.

The binding chamber 15 harbors on one side the solid phase 14 and on the other side provides fluidic connections for processing the process fluids through the solid phase 14. The binding chamber 15 generally has an inlet and an outlet and the solid phase 14 is located in between. The shape of the inlets and outlets are preferably designed in an optimal manner to allow the fluid to flow in respectively out of the solid phase 14. The binding chamber 15 can have various shapes, e.g. a cylindrical shape with a diameter from 1 mm to 20 mm, more preferred from 2 mm to 12 mm, and a height of 0.1 mm to 10 mm, most preferred in a range from 1 mm to 5 mm. The volume ranges therefore from approx. 5 μl to 500 μl and is most preferred in a range of 10 μl to 200 μl.

The amplification and detection chamber 16 is designed to optimally perform the amplification/detection step. In case of PCR, where thermal cycling is required at least one wall should allow heat transfer. The heat transfer wall 41 is preferably located in the “main plane” of device 1, i.e. on a side-surface 50. In general, according to a preferred embodiment of the invention, the amplification chamber 16 is covered on one side with a heat transfer wall 41 having a good thermal conductivity for providing a direct or indirect thermal contact between a temperature control means of the nucleic acid analysis apparatus and the amplification chamber 16 for heating and/or cooling of a sample in the amplification chamber 16 of the device when it is operated in the nucleic acid amplification apparatus.

Figure 6:
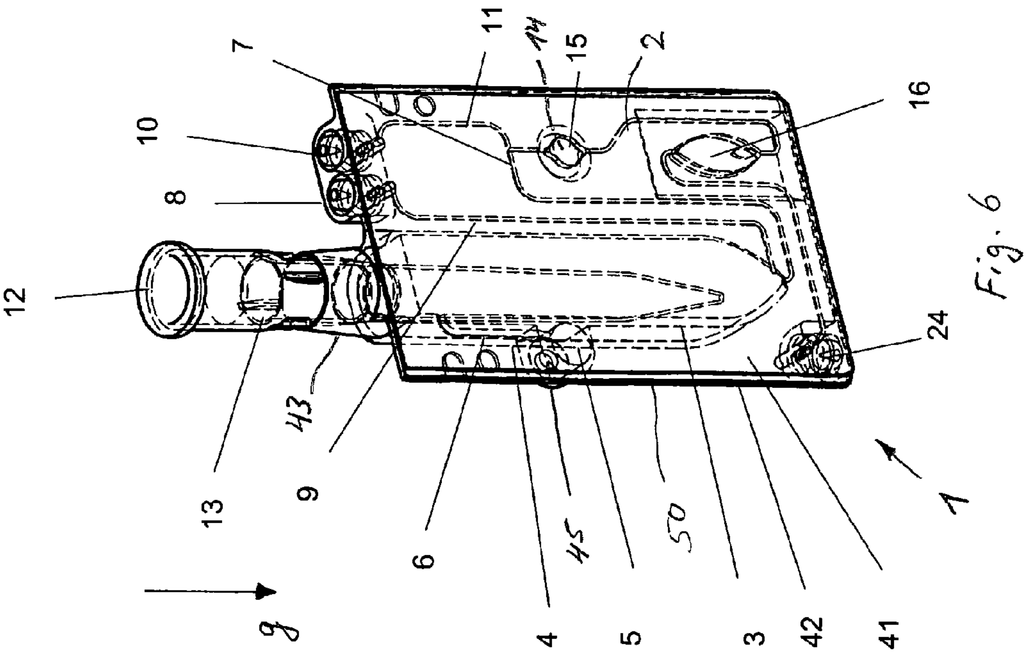
FIG. 6 shows a more detailed perspective back view of the disposable according to FIG. 3.
Figure 7:
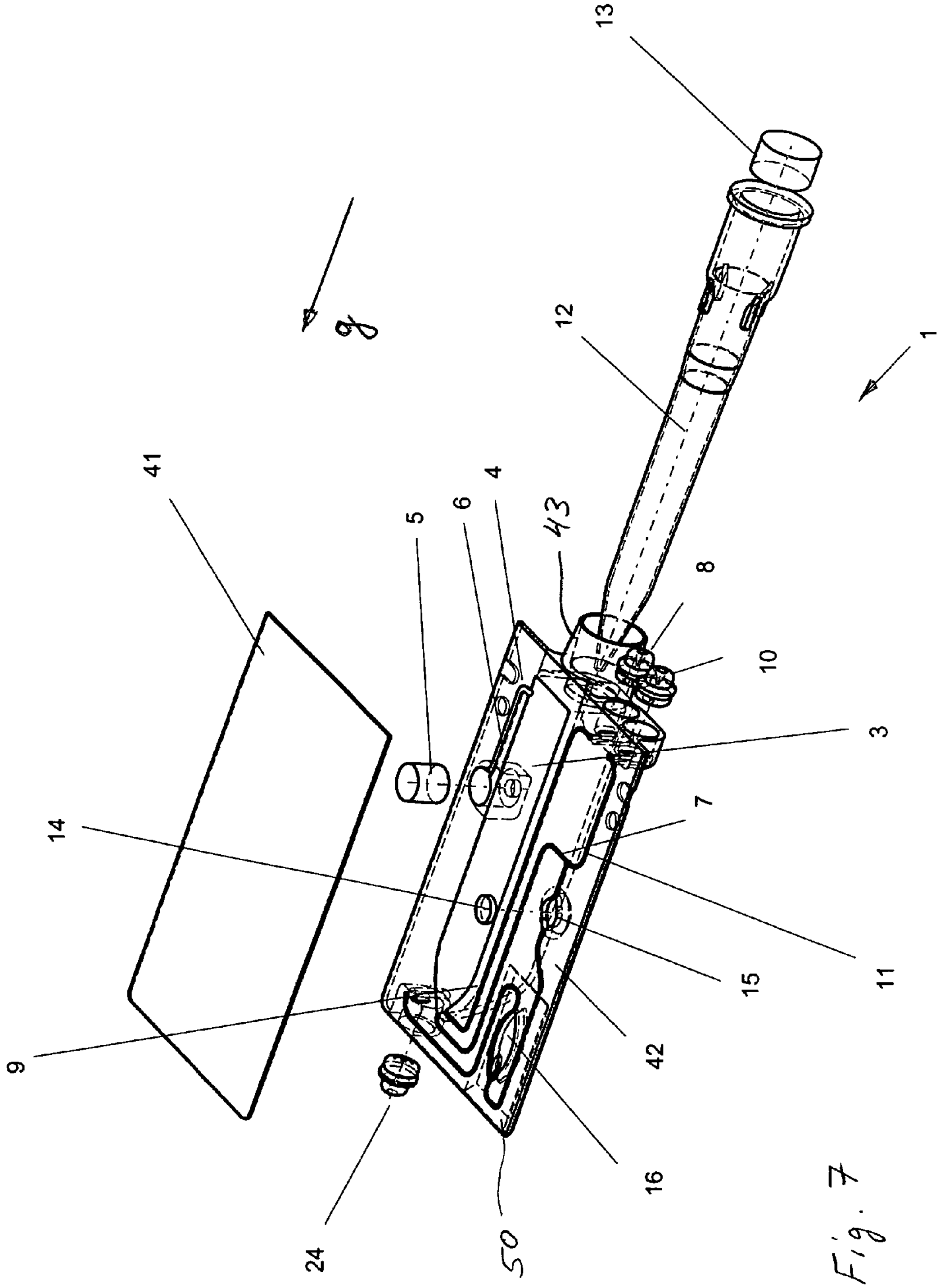
FIG. 7 shows an exploded view of the parts of the disposable according to FIG. 3 to the back-side of the disposable.

According to another preferable embodiment the effective direction of heat flow between the temperature control means of the nucleic acid amplification apparatus and the amplification chamber 16 is horizontal and perpendicular in regard to the plane of the heat transfer wall, i.e. the heat flow direction is perpendicular in regard to the heater surface being in contact with the heat transfer and sealing foil of the amplification chamber 16. This allows a good thermal coupling with a big surface over a short distance and also requires only little space in the apparatus.

Where optical detection is required at least one wall of the chamber 16 has a sufficient transparency, i.e. comprises a transparent optical measurement window. According to a preferred embodiment a transparent optical measurement window of the amplification chamber 16 and the heat transfer wall 41 are arranged on opposite sides of the amplification chamber 16. In the embodiment illustrated in the figures the optical window of the amplification chamber 16 is on the front side (FIG. 5) and the heat transfer wall 41 is on the back side (FIG. 6). For filling/evacuation respectively ventilation the chamber has an inlet and an outlet. The chamber is designed in a manner not to generate carry over from one process step to another. According to another preferred embodiment a transparent optical measurement window is provided in the amplification chamber 16, wherein the measurement direction from the measurement window to an optical sensor of the nucleic acid amplification apparatus is horizontal.

In order to give a robust signal the optical detection area (=area observed by a detector during analysis) has a size of at least 1 mm$^2$, more preferred at least 4 mm$^2$. A most preferred range may be 5 mm$^2$ to 20 mm$^2$. Observing a larger area especially in case of a fluorescence measurement makes the fluorescence measurement less sensitive to e.g. bubbles occasionally observed.

A specific feature of the embodiment according to device 1 is that the fluid path (comprising at least some of the channels 44) is constructed in such a manner that all fluids passing through the binding chamber 15 also pass through the amplification chamber 16, as there is no bypass of the amplification chamber 16 that would allow a fluid leaving the binding chamber 15 to reach an outlet of the device 1 without passing through the amplification chamber 16. It has been found in the framework of the invention that this feature does not interfere with the requirement of a precise and reliable analysis if a suitable wash step of the amplification chamber is performed before the elution, amplification and detection is performed.

Typical volumes of this chamber 16 are in a range of 1 μl to 300 μl, most preferred in range of 5 μl to 200 μl. For fast heat transfers within the fluid the chamber 16 is thin and flat, and the wall on the flat side has a high heat conductivity. The thickness of the amplification chamber 16 in the direction of heat transfer is in the range of 50 μm to 5 mm, more preferred in a range of 100 μm to 2 mm and most preferred in a range of 200 μm to 1 mm. According to another general aspect it may be preferable when the volume of the amplification chamber 16 is larger than the volume of the binding chamber 15, but preferably not larger than twice the volume of the binding chamber.

According to a further preferable embodiment fluidic filling measurement means is provided in the outlet channel of the amplification chamber 16 close to the outlet of the amplification chamber for detecting a moment when the amplification chamber 16 has been filled or emptied completely. This may be helpful to monitor the nucleic analysis process, e.g. in order to avoid loss of material to be detected in the amplification chamber 16 by leaving the amplification chamber 16 when it is filled by entering of this material or by entering of much of this material into the outlet channel of the amplification chamber 16. This feature is particularly advantageous in the binding step, wherein the binding solution is processed through the binding chamber 15, and in the elution step when the nucleic acids to be detected are transferred from the binding chamber to the amplification chamber 16.

The fluidic filling measurement means may be an optical transparent window within the disposable enabling optical detection of fluid in the outlet channel by a corresponding optical sensor of the nucleic acid amplification apparatus, e.g. by measurement of fluorescence, transmission, reflection, refraction or absorption, if required with the additional use of a mirror, or an electric sensor placed in or close to the outlet channel.

According to a preferred embodiment of the invention the inlet channel of the amplification chamber, the amplification chamber 16 and the outlet channel of the amplification chamber are arranged such in the device 1 that the liquid enters into the amplification chamber 16 through the inlet channel in an upward direction and leaves the amplification chamber through the outlet channel in an upward direction when the device 1 is operated in the nucleic acid analysis apparatus. In this case the complete and bubble free filling of the amplification chamber 16 is improved and no liquid is lost into the output channel before the amplification chamber 16 is filled completely.

Figure 8:
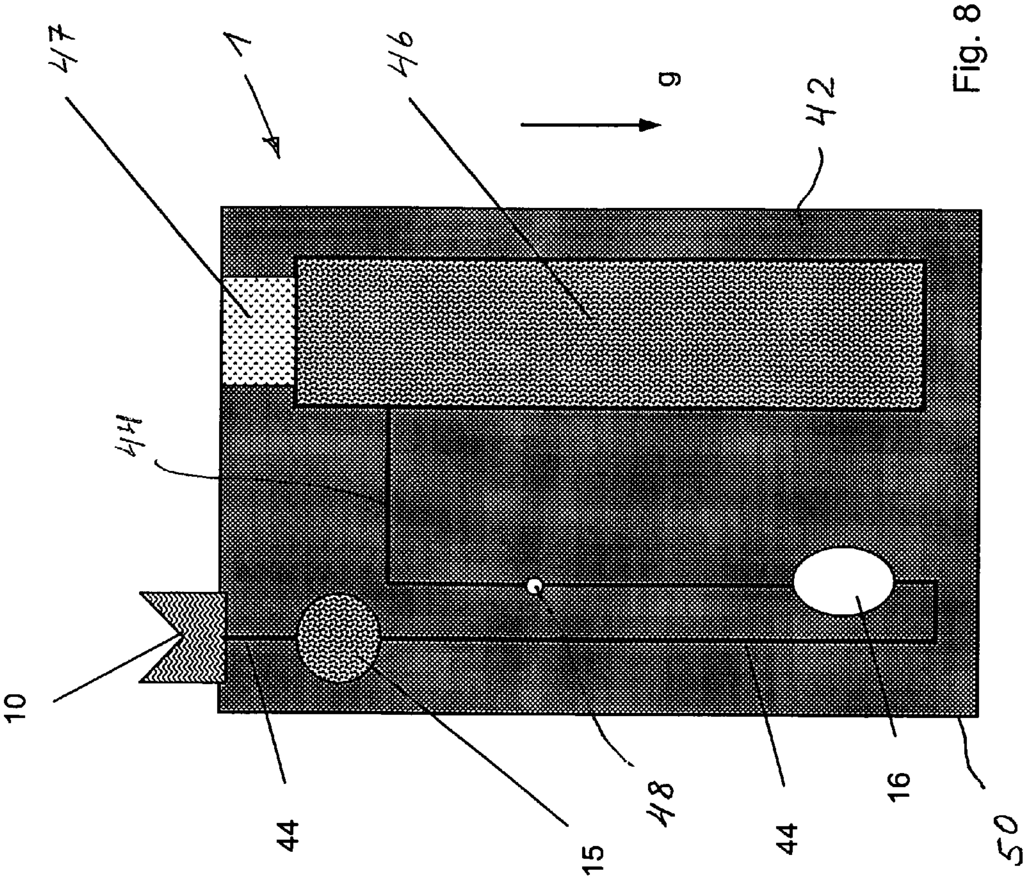
FIG. 8 shows a schematic front view of a first embodiment of a disposable with an integrated waste chamber and without a lysis chamber.
Figure 9:
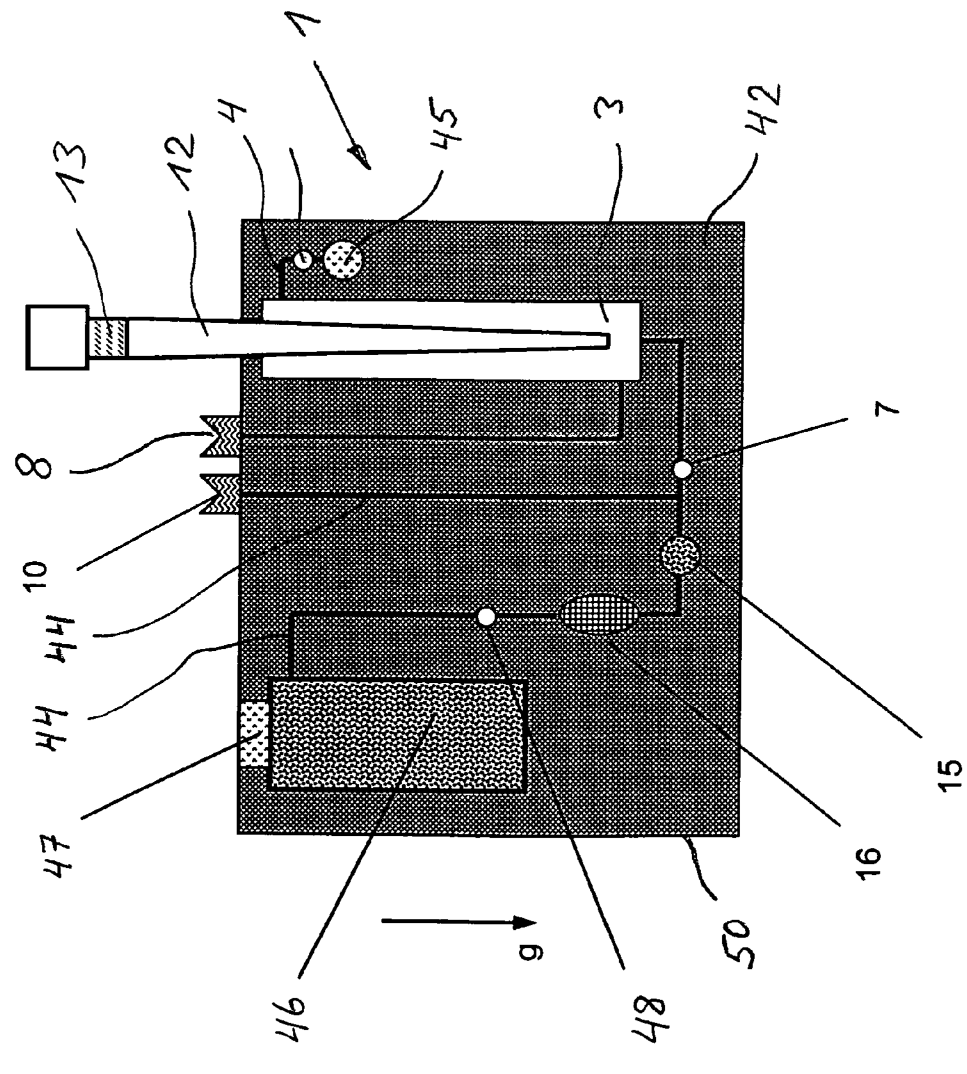
FIG. 9 shows a schematic front view of a second embodiment of a disposable with an integrated waste chamber and with a lysis chamber.

The waste connector 24 provides a fluidic connection of the disposable 1 to a waste container of the nucleic acid analysis apparatus into which the disposable 1 is inserted for operation and use. However, it is not mandatory to have a waste connector 24 on the device 1. In other embodiments which are schematically illustrated in FIGS. 8 and 9 the device 1 may comprise one or several waste chambers 46 integrated into the device 1 for taking up waste material resulting in the process performed with the device 1. The waste chamber 46 is preferably situated on a side-surface 50 of the body 42 and formed by a cavity being a recess in the body 42, and that side-surface 50 being covered by a wall 41, which wall 41 is substantially a vertical plane when the device 1 is operated in the nucleic acid amplification apparatus. In cases in which a waste chamber 46 is provided on the device 1 no waste connector 24 to a waste container external of the device 1 may be required. However, a venting mechanism, e.g. venting ports or a waste chamber ventilation 47, may in this case be suitable or required for enabling liquid to reach and enter into the waste chamber 46 then, and allowing gas to exit the waste chamber 46.

Further a sealing point 48 may be comprised for closing the channel 48 leading to the waste chamber 46. The waste chamber 46 has a volume to collect all liquid waste resulting out of the nucleic acid analysis process. Such waste liquids are e.g. processed binding solution and the used wash buffer. The volume is typically in a range of 0.2 ml to 10 ml, most preferred between 0.5 to 5 ml. The integrated waste chamber 46 may contain a hydrophilic, fleece like material, e.g. cotton or glass fibers to capillary adsorbe the waste fluids arriving in the waste chamber 46. For gas exchange (gas communication) between the interior of the integrated waste chamber 46 with the ambient the waste chamber 46 has an opening which allows gas exchange, i.e. ventilation of the waste chamber 46. The ventilation does not allow fluid or aerosol to pass through the ventilation-material (at normal operation). A same or similar material as in the tip 12 or for the lysis-chamber venting filter 5 is used, e.g. a porous plastic plug or a PTFE membrane.

The fluid port 8 serves as reagents inlet to the lysis chamber 3. The fluid port 10 serves as a fluidic supply interface connected by a fluid channel 44 to at least one of the binding chamber 15 and the amplification chamber 16, preferably to the inlet side of the binding chamber 15. The supply interface may located in the “main plane” of the device 1, i.e. in a plane corresponding to a side-surface 50, or in a parallel plane to the “main plane” and being adapted to be contacted by a fluid supply means of the nucleic acid amplification apparatus, wherein the fluid supply means is adapted to supply to the device 1 liquid like a sample or a reagent in a vertical direction of flow. The waste connector 24 serves as a fluidic removal interface connected by a fluid channel 44 to at least one of the binding chamber 15 and the amplification chamber 16, preferably to the outlet side of the amplification chamber 16, the removal interface being located in the “main plane” of the device 1, i.e. in a plane corresponding to a side-surface 50, or in a parallel plane to the “main plane” and being adapted to be contacted by a fluid supply means of the nucleic acid amplification apparatus, wherein the fluid supply means is adapted to remove from the device 1 liquid like a sample or a reagent in a vertical direction of flow, i.e. in a direction parallel to the side-surface 50 of the device 1. By this a small space is required for the disposables 1 and they can be stored and processed in a closed distance to one another.

For this purpose the analysis apparatus may comprise a reagent pipetting system for dosing a required reagent, generally by aspirating the reagent from a reagent container and dispensing it to the place where the reagent is used. The reagent pipetting system may comprise a reagent dosing fluid system and a reagent pipetting tip by which the reagent is aspirated respectively dispensed, e.g. an elongated hollow needle able to pick up a reagent from a reagent container and applying it to the place where the reagent is used.

Also a gas dosing system for delivering air (or an other gas, e.g. purified nitrogen) to the disposable 1 by an interface may be provided by the analysis apparatus. The system may deliver gas with constant pressure, various pressures and/or a predefined gas-volume. The system may need in a case where air is used an air filter. For the application of the gas a connecting element, able to interface to the point of application is required.

Further a sample dosing system may be provided by the analysis apparatus, i.e. a system able to aspirate respectively dispense a defined volume of sample or air to the disposable 1. Typically an air displacement syringe pump may be used.

An advantageous feature of the embodiment shown in FIG. 1 is that it comprises at least two fluidic supply interfaces, namely a first one for supplying a sample to the device 1, which is performed in the example show by the tip 12 into the lysis chamber 3, and a second one, e.g. fluid port 8 or 10, for supplying a reagent to the device 1. This embodiment is advantageous in that it helps to reduce contamination- and carry-over-problems.

According to preferred embodiments the fluidic supply connection elements of the disposable 1 are constructed such that a fluid can be supplied to the disposable 1 from above the disposable 1 in a downward direction and/or a fluid can be removed from the disposable 1 in an upward or downward direction. By this a small space is required for the disposables 1 and they can be stored and processed in a closed distance to one another.

For this purposes it is advantageous when the projection of the body 42 of the device 1 is basically a rectangle, i.e. the part of the device 1 lying in the side-surface 50 has preferably a basically rectangular shape (when viewed orthogonal to the side-surface 50 and the fluid supply interface and/or the fluid removal interface is located on the top or bottom of the rectangle and oriented such that the fluid supply and/or removal is performed oriented parallel to the plane of that rectangle, i.e. the side-surface 50 or main plane of the device 1.

The heat transferring wall 41 forms together with the body 42 (and together with inserted parts as septa, fleece and vents) an assembly of the disposable 1. The heat transferring wall 41 is joined to the body 42 in a manner that the resulting connection is fluidic tight. The open space formed between the body 42 and the heat transferring wall 41 forms channels and chambers. The joining techniques used to assemble the heat transferring wall 41 to the body 42 are commonly known. Typical and preferred joining techniques are laser welding, ultrasound joining, thermal bonding or sealing, and gluing.

The heat transferring wall 41 is generally a flat, sheet like material, or a thin layered body 42. The thickness of this element is typically in a range of 0.01 mm to 1 mm, most preferred in a range of 0.04 mm to 0.35 mm. The overall heat transfer rate of the heat transferring wall 41 is typically greater than 200 W/m2/K, more preferred greater than 2,000 W/m2/K. According to preferred embodiments the heat transfer wall 41 is a sealing foil, particularly a metallic foil or a foil comprising a metal sheet.

Because the heat transferring wall 41 is in contact with the reagents used for the assay and the reaction fluids, a similar inertness to the reaction is required as for the body 42, at least for those sections of this element which are in contact with the reagents or reaction fluids. A preferred material to be in contact with the reaction fluids or reagents is Polypropylene.

A preferred heat transferring wall 41 is a laminate formed by a polymer and a metal-layer. Where in the assembled status the polymer layer is the layer closer to the body 42 forming the material being in contact with the reagents and sample and where the metal layer is farer from the body 42 and is not in direct contact to the reagents and sample. A preferred laminate foil has a polymer-layer form 0.1 μm and 300 μm, most preferred between 0.1 μm and 80 μm and a metal layer with a thickness from 20 μm to 400 μm, most preferred within a range of 20 μm to 200 μm. A most preferred material to be joined to a polypropylene body 42 by thermal sealing is a laminate foil of 35 μm polypropylene and 100 μm aluminum, which are commercially available.

In a preferred embodiment the device 1 comprises a device body 42 having a structured surface for forming the cavities and a sealing cover 41 which covers the structured surface thereby forming a wall 41 covering a side-surface 50 of the device 1, e.g. of the amplification chamber 16 for performing nucleic acid amplification, and of an inlet channel 2 connected to the amplification chamber 16 for providing the amplification chamber 16 with sample liquid, wherein a first layer of the sealing cover 41 is made of a material which is inert with respect to the sample liquid, and a second layer of the sealing cover 41 which is made of a metal, preferably aluminium. The structured surface is preferably a side-surface 50 of the body 42.

The rigid body 42 is stiff and hard such that it has a fixed shape. It is typically made from a firm, stable, hard material, e.g. a single rather rigid plastic polymer. Preferred materials for NAT are as inert as required to the corresponding nucleic acid test or assay. Supplemental requirements may exist for the material as e.g. transparency, mechanical requirement, thermal requirements, etc. A most preferred material for the body 42 for many NAT assays is polypropylene. The body 42 may be produced in an injection molding process. When required also a two compound injection molding may be used to include thermoplastic elastomeric (TPE) elements in the injection molded part production process. In this manner for example inlets made from a thermoplastic elastomere, adhering to the body 42, may be included. The material thickness of the body 42 is preferably in the range of 0.3 mm to 4 mm, most preferred in a range of 0.5 mm to 1.5 mm. Preferable mechanical properties of the material are as follows: Tensile modulus (modulus of elasticity, Young's modulus) in the range from 0.1 to 5 GPa; tensile strength in the range from 10 to 200 MPa.

Grooves in body 42, which are covered during the production process of the integrated disposable 1 by the heat transferring wall 41, can form either chambers or channels. An increased stiffness of the body 42 without using thick walls can be achieved by using rips. According to a preferred embodiment the device may comprise a device body 42 and a cover which covers a surface of the device body, and wherein a fluid channel is provided as a groove in the surface of the device body covered by the cover which is fixed to the surface of the device body.

The sealing zone 43 is located between the body 42 and the sample pipetting tip 12. The sealing zone 43 is generated between the body 42 and the sample pipetting tip 12, when the tip is plugged into the corresponding opening in the disposable.

The channels 44 are fluid transport ways within the integrated disposable 1, generally formed between the body 42 and a second element covering a groove in the body 42, e.g. covered by the heat transferring wall 41. The cross section of a channel has an area in the range of 0.01 $mm^2$ to 2 $mm^2$, more preferred from 0.04 $mm^2$ to 0.5 $mm^2$.

Figure 10:
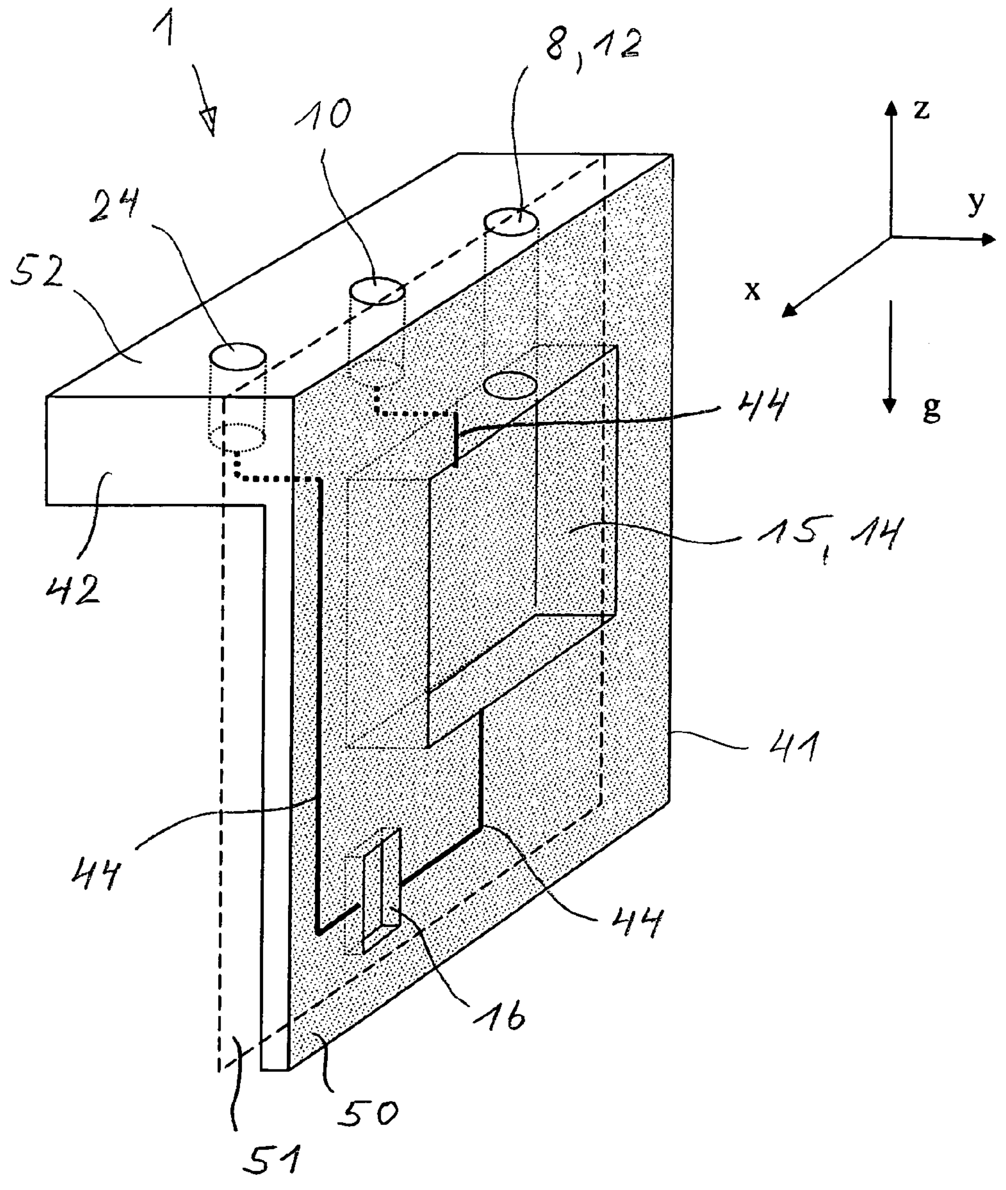
FIG. 10 shows a schematic perspective view of a third embodiment of a disposable according to the invention.
Figure 11:
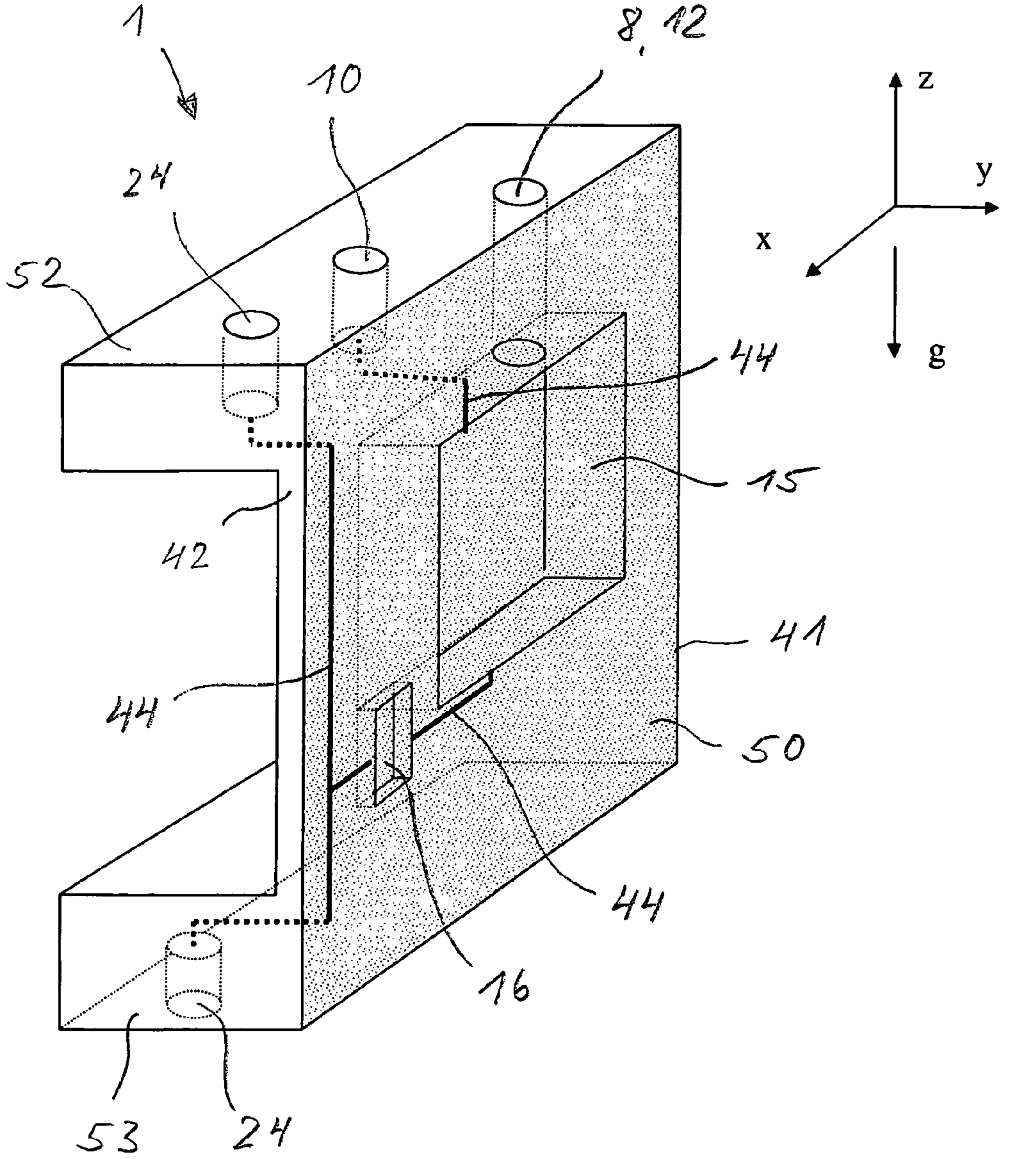
FIG. 11 shows a schematic perspective view of a fourth embodiment of a disposable according to the invention.

FIGS. 10 and 11 illustrate in schematic perspective views basis principles of a disposable 1 according to the invention as described in the previous figures. These figures mainly serve to illustrate the side-surface 50 which comprises the binding chamber 15, a channel 44 and the amplification chamber 16. In the figures only one side-surface 50 is shown, namely on the right side of the body 42. Another structured side-surface is or may be comprised on the left side 42 of the body 42, i.e. parallel and opposite to the side-surface 50 shown. Of course, the chambers and the channels have a non zero extension in a direction perpendicular to the side-surface 50, i.e. the y-direction, because they are constructed as cavities extending from the side-surface 50 into the body 42. A part of these elements, i.e. a section of these elements is preferably located in the side-surface 50. The z-direction of the side-surface 50 is opposite to the direction of gravity g when the device 1 is operated in a nucleic acid amplification apparatus, i.e. the side-surface 50 is oriented in a vertical direction.

The fluid paths are placed in a parallel plane 51 (shown only in FIG. 10) which is parallel and preferably in a close or zero distance to the side-surface 50. The embodiment of FIG. 10 comprises fluid ports only on the top of the device 1 and the embodiment of FIG. 11 comprises fluid ports on both the top and bottom side of device 1. As can be seen in FIGS. 10 and 11 the fluid ports on the top side of the device 1 are located also in a horizontal fluid interface top plane 52 which is a plane in x-y-direction. Correspondingly, as can be seen in FIG. 11, the fluid port at the bottom side of device 1 is located in a horizontal fluid interface bottom plane 53. Generally expressed it may be favorable when the device 1 comprises at least one fluid interface plane 52, 53 orthogonal to the plane 50, i.e. fluid interface plane 52, 53 is a horizontal plane, wherein from this plane channels 44 lead away in the side-surface 50 or the parallel plane 51 to the various chambers 3, 15, 16 of the device 1. In this plane 52, 53 the fluid interfaces 8, 10, 24 may be located and e.g. septa may be inserted into holes located in these horizontal planes which are designed to accommodate the septa.

The individual steps of a typical procedure according to FIG. 1 with a device 1 according to FIGS. 3 to 11 are described as follows:

Step 1: Lysis and Preparation of the Binding Solution

The purpose of the first step in the sample preparation process is making the NA ready for binding. This may include a digestion/degradation of undesired mater, e.g. the digestion of the protein shell of a virus by a proteinase, and/or disrupting cell-walls of a bacterium by detergents. Another purpose of this step is adapting the conditions (ambient solution of the analyte) so that the analyte NA can bind to the solid phase in the following binding step (adjusting binding conditions).

The procedure of step 1 may comprise the following steps:

- Transfer of an integrated disposable 1 from an integrated disposable device delivery rack to a sample preparation station by means of a disposable device gripper and an automated transfer system. According to a preferred embodiment of the invention the body 42 of the device 1 comprises a guidance for guiding the device 1 in the nucleic acid amplification apparatus and/or a gripping interface for gripping the device 1 by an actuation and handling means of the nucleic acid amplification apparatus in order to support this process step.
- Gripping up a sample pipetting tip 12 by a tip gripper mounted on the automated transfer system. The sample pipetting tip is interfaced by the tip gripper. The tip gripper is connected to an air operated sample dosing system.
- The sample is aspirated by the sample dosing system from a sample tube or other container containing the sample.
- The automated transfer system moves then the aspirated sample in the sample pipetting tip 12 to the integrated disposable 1.
- The transfer system locks then the sample pipetting tip to the lysis chamber 3 of the disposable 1.
- A sample dosing system doses then the sample to the lysis chamber 3.
- Reagents used for the preparation of the binding solution are successively added to the integrated disposable 1 by aspirating the reagents from reagents containers containing the reagents and dosing them into integrated disposable 1. The reagents for preparing the binding solution are added to the process using a reagent pipetting system having a reagents pipetting tip, a reagents dosing fluid system and a reagents pipetting tip wash station, being mounted on a automated transfer-system. The reagents for the lysis and preparation of the binding solution are dosed to the fluid port 8 of the disposable having a fluidic connection 9 to the lysis chamber 3.
- The reagents added to the sample present in the lysis chamber 3 are mixed by a sip and spit process. The sip and spit process is executed by aspirating respectively dispensing fluid from the lysis chamber 3 into the sample pipetting tip 12 respectively backwards from the sample pipetting tip 12 to the lysis chamber 3. For gas exchange of the lysis chamber 3 it has a lysis chamber venting system 4. For the sip and spit mixing the tip gripper connects to the sample pipetting tip 12 and doses respectively aspirates air by means of the sample dosing system.
- For thermal control of the process the lysis chamber 3 is connected to a thermal control system. Heat is transferred by the heat transferring wall 41.
- For contamination control the sample pipetting tip 12 contains a tip filter 13 and the lysis chamber venting system 4 leads through a lysis chamber venting filter 5 protecting the environment from contamination respectively protecting the process from contaminations out of environment.

The following example is given for step 1:

- 25 µl QS is dosed to the lysis chamber 3 through the fluid port 8 and the fluid connection 9.
- 630 µl EDTA plasma (=sample from a patient) is pipetted by the automated transfer system. The sample can be spiked for control reasons with a HBV control (e.g. with 10,000 copies (=10 kcp) of HBV virus e.g. from Acrometrix). For pipetting the sample pipetting tip 12 is used to aspirate the volume out of the sample tube and transfer it to the integrated disposable 1 by means of the automated transfer system. The sample and the QS are mixed by sip and spit mixing (2×) using the air dosing system.

65 µl Proteinase is dosed to the reaction through the fluid port 8 using the reagent pipetting system.

- The Proteinase is completely mixed by five sip and spit mixing steps and the reaction mix is thermostaticed to 37° C. using the thermal control system and incubated for 300 seconds.
- After this incubation 1420 µl lysis buffer is dosed through the fluid port 8 to the reaction mix and is mixed completely mix by four sip and spit mixing steps.

Step 2: Binding

The purpose of the second step is to bring the prior prepared binding solution in contact or process it over a solid phase 14 able to bind the NA sufficiently selective and sufficiently quantitative. Inhibiting compounds present in the binding solution are either not bound or bound in negligible amounts or bound compounds are eliminated in one or several later wash steps.

The procedure may of step 2 may comprise the following steps:

- Principally all known fluid transport mechanisms are useable to process the binding solution through the binding chamber 15. Examples of such fluid transport mechanisms are:
  - Direct pumping, e.g. by a piston pressing the binding solution through the binding chamber 15.
  - Direct pumping e.g. by compressing the solution harboured in chamber by deformation of a flexible wall of the lysis chamber 3.
  - Pumping using the hydrostatic pressure caused by gravity force.
  - Pumping using hydrostatic pressure caused by centrifugal force.
  - Applying a differential pressure by applying a gas pressure on one side and/or vacuum on the other side of the system.

Depending on the design of the system fluid paths must be switched for enabling and/or controlling the direction of fluid flows. e.g. in case of applying pressure to the binding solution a lysis chamber venting system 4 must be closed, or a flow path leading from the lysis chamber 3, through binding chamber 15, through the amplification and detection chamber 16, through the waste connector 24 and finally leading to a waste container must be enabled e.g. by opening a waste valve.

Supplemental means as e.g. a fluid presence sensor may control the process in respect to timing and process conformity.

The following example is given for step 2:

The lysis chamber venting system 4 is closed by sealing of a narrow channel by thermally sealing off the channel 44 by a channel sealing equipment. A piston having a temperature of 300° C. is pressed with a force of 30 N to the channel section that has to be sealed (sealing point 6) for 15 sec.

The connection to the waste is made by the waste connector 24.

The waste valve of the apparatus is opened.

A tip gripper connects to the sample pipetting tip 12 and pressurizes the binding solution to +1 bar (above ambient pressure).

By the application of this differential pressure the prior prepared binding solution present in the lysis chamber 3 flows out of the lysis chamber 3 through a channel 44 located at the lower end of the lysis chamber 3, through the binding chamber 15. The binding chamber 15 harbours as solid phase 14 a disk of 5 mm diameter of a glass fibre fleece (220 g/m$^2$, quality as used in the "High-Pure"-products of Roche Applied Science). The binding chamber 15 has a diameter of approx. 5 mm and a height of 1 mm. The channels 44 leading to/from the binding chamber 15 have a maximal width of 0.6 mm and height of 0.6 mm.

The binding solution flows after the binding chamber 15 through the amplification and detection chamber 16 to the waste.

After binding (the time is observed by a fluid presence sensor) the pressure is turned off. A typical binding time is in the range of 2 min.

Step 3: Wash

In step 3 residues of binding solution present in the interspace of the solid phase 14 absorber and material absorbed to the solid-phase but being dissolvable from the solid phase 14 in the wash buffer is removed, and walls of the integrated disposable 1 being contaminated by the binding solution are washed in this step.

The procedure of step 3 may comprise the following steps:

Prior to processing (pumping) the wash buffer trough the system on the integrated disposable device 1 that has to be washed, depending on the design of this fluid system, the flow paths have to be switched for enabling-and/or controlling the direction of fluid flow, e.g. the fluid path leading from the lysis chamber 3 to the binding chamber 15 has to be disabled to avoid backflow of wash buffer to the lysis chamber 3 and the flow path leading from binding chamber 15, through the amplification and detection chamber 16 and leading finally to the waste container of the analysis apparatus has be enabled e.g. by opening a waste valve.

The wash buffer is aspirated from a reagent container containing the wash buffer and pumped through the fluid section in the integrated disposable 1 which has to be washed. For processing the wash buffer the reagent pipetting system having a reagents pipetting tip and a reagents dosing fluid system a reagents pipetting tip wash station is used. The wash buffer for washing the system that has to be processed to a fluid port 10 having a fluidic connection 11 leading to the binding chamber 15 respectively having a fluidic connection to the complete fluid system on the integrated disposable 1 that has to be washed.

When required several wash steps with the same or with various wash buffers can be carried out.

The wash step can be carried out under thermal control due to the connection of the integrated device to a thermal control system of the apparatus.

The following example is given for step 3:

The channel leading from the lysis chamber 3 to the binding chamber 15 is closed by thermally sealing off the channel by a channel sealing equipment. A piston having a temperature of 300° C. is pressed with a force of 30 N towards the channel section that has to be sealed (sealing point 7) for 15 sec.

The waste valve in the apparatus is afterwards opened.

600 µl wash buffer are aspirated from the corresponding reagents container using a reagent pipetting system. 500 µl are then dosed at a flow rate of 1800 µl/min to the fluid port 10. The wash buffer flows through the binding chamber 15 and the amplification and detection chamber 16 to a waste container connected to the waste connector.

Step 4: Wash-Removal/Dry

This process step 4 applies to arrangements of integrated devices and reagents where the wash buffer has an inhibiting effect to the following process steps (mainly to the step of NA-detection). In these cases the wash buffer in the integrated disposable 1 has to be removed or reduced below a critical level.

The following principles alone or in combination are used for the wash buffer removal.

Fluid mechanical displacement (e.g. by gas e.g. air or by an other neutral fluid).

Drying off evaporable elements of the wash buffer which are know to inhibit the following process steps by means of heating and/or simultaneous pumping a gas through the section of the integrated disposable 1 wherefrom wash buffer has to be removed.

Chemical neutralization by processing a solution through the integrated disposable 1 able to neutralize the inhibiting potential of a wash buffer.

The procedure of step 4 may comprise the following steps:

For fluid mechanical displacement and drying off evaporable elements of the wash buffer an air dosing system (or other gas) is used.

To reduce the process time of drying off the evaporable compounds of wash buffer, the integrated disposable 1 is connected to a temperature control system allowing this step to be carried out at an elevated temperature.

An air dosing system is automatically connected to the fluid port 8 of the integrated disposable 1 which is connected to the fluid system in the device wherefrom the wash buffer has to be removed.

The flow path leading from fluid port 10, through the binding chamber 15, through the amplification and detection chamber 16 and finally leading to a waste container has to be enabled, e.g. by opening a valve.

For fluid mechanical displacement and drying of evaporable parts of the wash buffer during a predefined process time, at predefined temperature and at a predefined pressure air is pumped through the system in the integrated disposable 1 wherefrom the wash buffer has to be removed.

The following example is given for step 4:

An air dosing system connects to the fluid port 10.

A waste valve is opened.

The integrated disposable 1 is thermostatized to 40° C..

Air is dosed for 15 seconds through the device 1. The pressure of the air is +1 bar (above ambient pressure)

After 15 seconds the temperature of the temperature control system is set to 50° C., and held for 20 sec.

The air dosing system then pumps air having a +1 bar pressure for 120 sec. through the integrated disposable 1 wherefrom the wash buffer has to be removed, while the temperature is kept at 50° C..

Step 5: Elution

In step 5 the NAs (selectively and quantitatively enough) adsorbed to the solid phase 14 and washed, are eluted (i.e. solved from the solid phase) prior to the final amplification and/or detection step. For reasons of simplicity the elution is made directly with detection reagents used for the following amplification and detection step. In the following context a combined [elution-buffer]+[PCR Mastermix]="EMMx" is used for this process.

In this process step 5 the NAs are eluted (solved) from the solid phase 14 in the EMMX and transferred to the amplification and detection chamber 16.

The procedure of step 5 may comprise the following steps:

The EMMx is dosed through the fluid port 10 to the integrated disposable 1.

The flow path leading from fluid port 10 through the binding chamber 15, through the amplification and detection chamber 16 and finally leading to a waste container has to be enabled, e.g. by opening a waste valve.

For thermal control of this process the integrated device is connected to thermal control system.

The elution step can comprise several sub steps, where the integrated device 1 is thermally controlled to a first temperature, where a first volume of EMMx is dosed to the system, where it is then incubated for a certain time and where at last a second volume is dosed.

Typically a first volume of EMMx fills the fluidic connection 11 including the binding chamber 15 containing the solid phase 14 and after a short incubation time, a second volume is dosed to the fluidic connection 11 transferring the eluate present in the binding chamber 15 to the amplification and detection chamber 16.

The following example is given for step 5:

The device is thermostatized by means of a thermal control system to 50° C. and held there for the whole process.

The waste valve connected to the waste connector 24 is opened.

By means of a reagent pipetting system 100 μl EMMx is aspirated.

A first volume of EMMx of 40 μl is dosed by the reagent pipetting system through the fluid port 10 at a flow rate of 1200 μl/min. In this first step only the solid phase 14 is wetted by the EMMx.

The integrated device 1 is incubated for 10 seconds

A second volume of EMMx of 42 μl is dosed by the reagent pipetting system through the fluid port 10 at a flow rate of 750 μl/min. The EMMX present in the amplification and detection chamber 16 containing the eluted NAs is transferred to the amplification and detection chamber 16.

Step 6: Amplification and Detection

After the above described, precedent process steps the analyte(s) are ready to be analyzed in step 6. To be analyzed means in this context: to be checked for the presence or absence of an analyte and/or optionally for detecting the concentration of the analyte(s).

The present invention is not limited to a distinct method of analyzing a NA. Higher amounts of analyte NA may be directly accessible to a method detecting the presence and optionally the concentration of the analyte. Lower and lowest concentrations of an analyte may require a so called "analyte amplification". For the substance class of NAs there exist several such biochemical analytical methods allowing the multiplication of the target analyte molecule or derivatives there off. By means of these methods copies or copies of derivatives of the analyte are generated, which are then much easier to detect due to their higher concentration after this analyte amplification.

Examples of such analytical methods for analyte amplification are:

- Polymerase Chain Reaction (PCR): The complementary DNA is generated by means of a DNA-Polymerase (e.g. DNA-Polymerase form Thermus aquaticus) using thermal cycling.
- Reverse Transcription Polymerase Chain Reaction (RT-PCR): Starts form a target RNA analyte, where prior to PCR a reverse transcripted c-DNA is generated by a reverse transcription enzyme.
- Ligase Chain Reaction (LCR): In this case (complementary) copies of the analyte DNA are created by ligation of fragments of the analyte DNA using a DNA-Ligase enzyme.
- RNA-polymerisation: In this case multiple c-DNA copies of the RNA analyte are created by multiple reverse transcriptions using a Reverse Transcription Enzyme.
- Strand displacement Amplification (SDA): Using combined polymerase chain reaction and strand displacement of prior synthesized copies. Uses beside the DNA-Polymerase-Enzyme a DNA-Nicking-Enzyme to create new start points for repeated replication steps.
- Rolling cycle amplification: Using a cyclic DNA primer.
- . . . any many others, as Ribo-SPIA®, LAMP, Helicase dependent PCR The use of the present invention is not limited to a distinct amplification and detection method. The amplified analyte(s) or derivative there off is either during the process of amplification or after amplification accessible to a detection method. The current invention is not limited to a distinct method of detecting the amplified NAs.

Examples of such detection methods for the amplified analyte (=amplicon) are:

- "Real-time" methods detecting the generation of amplified analyte (or derivative) during the amplification:
  - Detection of an amplicon using Taqman probes, which are specific probes being digested by the Polymerase in case of the presence of the addressed analyte forming an unquenched fluorescence.
  - Detection of an amplicon using hybridization probes, where amplicon-specific hybridization-probes hybridize to the amplicon and thereby changes a spectroscopic property.
  - Detection of amplicon using ds-DNA interchelators (e.g. Picogreen®), where those interchelator molecules have an affinity to the formed ds-DNA amplicon and changes its spectroscopic properties in the presence of the ds-DNA.

Detection of amplicon using a reflexion or turbity measurement (e.g. in case of LAMP amplification where large amplicons are produced)

. . . and many others.

Post amplification detection methods

Gel electrophoresis: detecting the formed amplicon

Hybridization of the amplicon to immobilized probes and detecting this hybridization by appropriate means . . . and many others The following example is given for step 6:

The integrated disposable 1 is transferred to a detection station comprising a thermal cycler for performing the PCR reaction and fluorescence measurement means to detect the formation of the amplicon resp. to detect the hydrolysed TaqMan® probes.

The following thermal cycling program is executed:

| | | | |
|---|---|---|---|
| | | 1cycle: | |
| | 50° C. | 120 sec | UNG-Step |
| | | 5 cycles: | |
| +2.5° C./sec | 95° C. | 15 sec | Denaturation |
| −2.0° C./sec | 59° C. | 50 sec | Annealing & fluorescence measurement after 30 sec |
| | | 45 cycles: | |
| +2.5° C./sec | 91° C. | 15 sec | Denaturation |
| −2.0° C./sec | 52° C. | 50 sec | Annealing & fluorescence measurement after 30 sec |

In total 50 fluorescence readings are made per analysis.

The target analyte (if present) generates fluorescence with an excitation wavelength of 485 nm (bandwidth 20 nm) and an emission at a wavelength of 525 nm (bandwidth 20 nm).

The QS is detected with second fluorphore having the excitation wavelength of 540 nm (bandwidth 20 nm) and an emission wavelength of 575 nm (bandwidth 20 nm). For a valid result the QS has to appear to certify the overall quality of the process and reagents (internal quality standard). Superior the QS can by used for quantification calculations of the analyte.

After analysis the integrated disposable 1 is discharged or unloaded or post PCR processed when required (e.g. for genotyping).

Step 7: Result Generation

In step 7 the signal measured in the detection step is converted to an information which is useful to the user, e.g. to a health status information (e.g. a viral load of a patient).

The following example is given for step 7:

All crude data (e.g. fluorescence data) received from the detection means are post-processed by an automated system (computer).

The QS curve is examined to conformity. This is done by comparison of the QS curve with an expected QS curve. Alternatively derivated characteristics of the curve may be used, e.g. the amount of signal formed at the end of the analysis and the "elbow-value", i.e. the cycle in which the fluorescence has reached a predefined relative fluorescence signal (e.g. 15% of the final fluorescence signal). A non conform QS signal may be used to detect non conform analysis.

The target "elbow-value" is calculated. The elbow value is generally related to the concentration.

From a corresponding calibration curve or reference data the concentration of the analyte is then calculated and reported to a user.

REFERENCE NUMERALS

1 integrated disposable sample holding and processing device
2 fluid channel
3 lysis chamber
4 lysis chamber venting system
5 lysis chamber venting filter
6 venting sealing point
7 closing sealing point
8 first fluid port
9 fluidic connection
10 second fluid port
11 fluidic connection
12 sample pipetting-tip
13 tip filter
14 solid phase
15 binding chamber
16 amplification and detection chamber
24 waste connector
41 heat transferring wall
42 body
43 sealing zone
44 channel
45 venting port
46 integrated waste chamber
47 waste chamber ventilation
48 waste chamber sealing point
50 side-surface
51 parallel plane
52 fluid interface top plane
53 fluid interface bottom plane
101 inlet
102 outlet
g gravity

The invention claimed is:

1. A disposable device capable of holding and processing samples for being operated in a nucleic acid amplification apparatus, comprising:

a rigid body comprising a top surface and a bottom surface oriented in a substantially vertical plane, a top surface, and a bottom surface, a binding chamber comprising a first cavity recessed into the top surface of said rigid body and containing a solid phase for solid phase extraction of a component of a sample to be analyzed, an amplification chamber comprising a second cavity recessed into the top surface of said rigid body, a sample preparation chamber comprising an elongated concave cavity recessed into the top surface of said rigid body and comprising a cylindrical opening situated below the vertical plane of the rigid body, the cylindrical opening configured to receive a sample transfer tip, the sample preparation chamber further comprising a venting system having a fluidic connection between the sample preparation chamber and the ambient allowing gas exchange, at least a first fluid channel leading from the binding chamber to an inlet port, the first fluid channel comprising a first sealing point configured to deform in its width from an open position to a closed position sealing together opposite walls of the first fluid channel interrupting flow of liquid or gas through said first fluid channel, at least a second fluid channel connecting said amplification chamber to said binding chamber, the second fluid channel comprising a second sealing point configured to deform in its width from an open position to a closed position sealing together opposite walls of the second fluid channel interrupting flow of liquid or gas through said second fluid channel, and at least one fluid interface connected by another fluid channel to at least one of the binding chamber and the amplification chamber, wherein the fluid interfaces are situated on at least one of the top and bottom-surfaces of the rigid body when the device is operated in the nucleic acid amplification apparatus, wherein:

each of said surfaces, on which a channel, the binding chamber or the amplification chamber is situated, is covered by at least one wall, and the surfaces are oriented along substantially vertical planes when the device is operated in the nucleic acid amplification apparatus.

2. The device according claim 1, wherein at least one fluid interface is effective to contact fluid delivery and/or fluid removal means of the nucleic acid amplification apparatus.

3. The device according to claim 2, wherein at least one fluid supply interface of the device is constructed such that a fluid is supplied to the device from above in a downward direction when the device is operated in the nucleic acid amplification apparatus.

4. The device according to claim 1, wherein the rigid body has a structured surface on which the cavities are formed, and a sealing cover which covers the structured surface thereby forming a wall covering a side-surface of the device, wherein:

a first layer of the sealing cover is made of a material which is inert with respect to the sample liquid, and a second layer of the sealing cover is made of a metal,

5. The device according to claim 1, wherein the amplification chamber is covered on one side with a heat transfer wall for providing a thermal contact between a temperature control means of the nucleic acid analysis apparatus and the amplification chamber for heating and cooling of a sample in the amplification chamber of the device when it is operated in the nucleic acid amplification apparatus.

6. The device according to claim 5, wherein an effective direction of the heat flow between the temperature control means and the amplification chamber is horizontal and perpendicular in regard to the plane of the heat transfer wall.

7. The device according to claim 4, wherein a transparent optical measurement window of the amplification chamber and the heat transfer wall are arranged on opposite sides of the amplification chamber.

8. The device according to claim 1, wherein a fluidic filling measurement means is provided in an outlet channel of the amplification chamber close to the outlet of the amplification chamber for detecting a moment when the amplification chamber has been filled or emptied completely.

9. The device according the claim 8, wherein the fluidic filling measurement means is an optical transparent window enabling optical detection of fluid in the outlet channel by a corresponding optical sensor of the nucleic acid amplification apparatus or an electric sensor placed in or close to the outlet channel.

10. The device according to claim 1, wherein the volume of the amplification chamber is larger than the volume of the binding chamber and not larger than twice the volume of the binding chamber.

11. The device according to claim 1, wherein the body of the device comprises at least a third sealing point configured to deform in its width from an open position to a closed position sealing together opposite walls of a third fluid channel interrupting flow of liquid or gas through said third fluid channel, said third fluid channel leading from a chamber of the device to an outlet port or venting port of the device, or leading from a first chamber to a second chamber.

12. The device according to claim 1, comprising at least one waste chamber integrated into the device for taking up waste material resulting in a process performed with the device, wherein the waste chamber is situated on a side-surface of the body and is formed by a cavity being a recess in the body, and that side-surface being covered by a wall, which wall is substantially a vertical plane when the device is operated in the nucleic acid amplification apparatus.

13. A system comprising at least one device according to claim 1 and a nucleic acid amplification apparatus for analyzing said device.

* * * * *

UNITED STATES PATENT AND TRADEMARK OFFICE

CERTIFICATE OF CORRECTION

PATENT NO. : 8,642,293 B2
APPLICATION NO. : 12/373517
DATED : February 4, 2014
INVENTOR(S) : Sarofim et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 631 days.

Signed and Sealed this
Twenty-ninth Day of September, 2015

Michelle K. Lee
*Director of the United States Patent and Trademark Office*